US006852739B1

(12) United States Patent
Garvey et al.

(10) Patent No.: US 6,852,739 B1
(45) Date of Patent: Feb. 8, 2005

(54) METHODS USING PROTON PUMP INHIBITORS AND NITRIC OXIDE DONORS

(75) Inventors: David S. Garvey, Dover, MA (US); L. Gordon Letts, Dover, MA (US); Sang William Tam, Dover, MA (US)

(73) Assignee: Nitromed Inc., Lexington, MA (US)

( * ) Notice: Subject to any disclaimer, the term of this patent is extended or adjusted under 35 U.S.C. 154(b) by 0 days.

(21) Appl. No.: 09/512,829

(22) Filed: Feb. 25, 2000

Related U.S. Application Data
(60) Provisional application No. 60/122,111, filed on Feb. 26, 1999.

(51) Int. Cl.[7] .................. C07D 401/12; A61K 31/4184

(52) U.S. Cl. .................. 514/338; 514/254.03; 514/361; 514/233.2; 514/300; 514/303; 514/260; 544/368; 544/134; 544/127; 544/324; 544/323; 544/284; 546/273.7; 546/121; 546/112; 546/115; 546/118; 548/126

(58) Field of Search .......................... 514/338, 254.03, 514/361, 233.2, 300, 303, 260; 544/368, 134, 127, 324, 323, 284; 546/273.7, 121, 112, 115, 118, 126

(56) References Cited

U.S. PATENT DOCUMENTS

| | | | |
|---|---|---|---|
| 4,045,563 A | 8/1977 | Berntsson et al. | |
| 4,255,431 A | 3/1981 | Junggren et al. | |
| 4,337,257 A | 6/1982 | Junggren et al. | |
| 4,359,465 A | 11/1982 | Ruwart | |
| 4,628,098 A * | 12/1986 | Nohara et al. | 546/271 |
| 4,634,710 A | 1/1987 | Fischli et al. | 514/338 |
| 4,758,579 A | 7/1988 | Kohl et al. | 514/338 |
| 4,806,549 A | 2/1989 | Ife et al. | 514/313 |
| 4,806,550 A | 2/1989 | Ife et al. | 514/313 |
| 4,808,596 A | 2/1989 | Matsuishi et al. | 514/303 |
| 4,818,760 A | 4/1989 | Binder et al. | 514/338 |
| 4,839,365 A | 6/1989 | Hirai et al. | 514/301 |
| 4,845,118 A | 7/1989 | Lang et al. | 514/338 |
| 4,871,734 A | 10/1989 | Lang et al. | 514/212 |
| 4,873,337 A | 10/1989 | Sih et al. | 546/271 |
| 4,956,366 A | 9/1990 | Nimmesgern et al. | 514/235.8 |
| 4,981,861 A | 1/1991 | Fischli et al. | 514/338 |
| 5,045,552 A | 9/1991 | Souda et al. | |
| 5,114,955 A | 5/1992 | Lang et al. | 514/338 |
| 5,149,702 A | 9/1992 | Yamada et al. | 514/303 |
| 5,380,758 A * | 1/1995 | Stamler et al. | 514/562 |
| 5,391,752 A | 2/1995 | Hoerrner et al. | |
| 5,403,830 A * | 4/1995 | Place | 514/184 |
| 5,439,917 A | 8/1995 | Briving et al. | 514/300 |
| 5,470,983 A | 11/1995 | Slemon et al. | |
| 5,554,631 A | 9/1996 | Kim et al. | 514/338 |
| 5,599,794 A | 2/1997 | Eek et al. | |
| 5,629,305 A * | 5/1997 | Eek et al. | 514/199 |
| 5,631,293 A | 5/1997 | Kleemann et al. | 514/563 |
| 5,641,792 A | 6/1997 | Kleemann et al. | 514/351 |
| 5,665,730 A | 9/1997 | Senn-Bilfinger et al. | 514/300 |
| 5,677,302 A | 10/1997 | Karimian et al. | 514/233.2 |
| 5,686,458 A | 11/1997 | Lee et al. | 514/260 |
| 5,703,073 A | 12/1997 | Garvey et al. | |
| 5,703,097 A | 12/1997 | Kim et al. | 514/338 |
| 5,714,504 A | 2/1998 | Lindberg et al. | |
| 5,750,531 A | 5/1998 | Lee et al. | 514/256 |
| 5,945,425 A | 8/1999 | Moormann et al. | 514/269 |
| 5,952,504 A | 9/1999 | Yoo et al. | 546/122 |
| 5,990,311 A | 11/1999 | Hong et al. | 544/324 |
| 6,323,234 B1 | 11/2001 | Garvey et al. | |

FOREIGN PATENT DOCUMENTS

| | | |
|---|---|---|
| EP | 0033094 | 8/1981 |
| EP | 0045200 | 2/1982 |
| EP | 0221041 | 5/1987 |
| EP | 0234485 | 9/1987 |
| EP | 0246774 | 11/1987 |
| EP | 0254588 | 1/1988 |
| EP | 0259174 | 3/1988 |
| WO | 8908104 | 9/1989 |
| WO | 9212969 | 8/1992 |
| WO | 9527714 | 10/1995 |

(List continued on next page.)

OTHER PUBLICATIONS

Beers et al., Crohn's Disease; Ulcerative Colitis, The Merck Manual of Diagnosis and Therapy, Seventeenth Edition, 1999.*
Sih et al, *J. Med. Chem.*, 34:1049–1062 (1991).
Brunton, Goodman and Gilman, The Pharmacological Basis of Therapeutics, 9th Ed., pp. 907–915 (1996).
Wallace et al, Journal of Gastroenterology and Hepatology, 9:S40–S44 (1994).
Barrachina et al, European Journal of Pharmacology, 281:R3–R4 (1995).

*Primary Examiner*—Deepak Rao
(74) *Attorney, Agent, or Firm*—Wilmer Cutler Pickering Hale & Dorr

(57) ABSTRACT

The present invention describes novel nitrosated and/or nitrosylated proton pump inhibitor compounds, and novel compositions comprising at least one proton pump inhibitor compound that is optionally substituted with at least one NO and/or $NO_2$ group, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one nonsteroidal antiinflammatory drug, selective COX-2 inhibitor, antacid, bismuth-containing reagent, acid-degradable antibacterial compound, and mixtures thereof. The present invention also provides methods for treating and/or preventing gastrointestinal disorders; facilitating ulcer healing; decreasing the recurrence of ulcers; improving gastroprotective properties, anti-*Helicobacter pylori* properties or antacid properties of proton pump-inhibitors; decreasing or reducing the gastrointestinal toxicity associated with the use of nonsteroidal antiinflammatory compounds; treating *Helicobacter pylori* and viral infections. The compounds and/or compositions of the present invention can also be provided in the form of a pharmaceutical kit.

32 Claims, 1 Drawing Sheet

FOREIGN PATENT DOCUMENTS

| | | | |
|---|---|---|---|
| WO | WO 96/24375 | * | 8/1996 |
| WO | WO 97/25064 | * | 7/1997 |
| WO | 9732854 | | 9/1997 |
| WO | 9818784 | | 5/1998 |
| WO | 9843968 | | 10/1998 |
| WO | 9857626 | | 12/1998 |
| WO | 9944595 | | 9/1999 |
| WO | 9945004 | | 9/1999 |
| WO | 9854172 | | 12/1999 |
| WO | WO 00/72838 A1 | | 12/2000 |
| WO | WO 02/00166 A2 | | 1/2002 |

* cited by examiner

METHODS USING PROTON PUMP INHIBITORS AND NITRIC OXIDE DONORS

RELATED APPLICATIONS

This application claims priority to U.S. Provisional Application No. 60/122,111 filed Feb. 26, 1999.

FIELD OF THE INVENTION

The present invention describes novel nitrosated and/or nitrosylated proton pump inhibitor compounds, and novel compositions comprising at least one proton pump inhibitor compound that is optionally substituted with at least one NO and/or $NO_2$ group, and, optionally, at least one compound that donates, transfers or releases nitric oxide, stimulates endogenous synthesis of nitric oxide, elevates endogenous levels of endothelium-derived relaxing factor or is a substrate for nitric oxide synthase, and/or at least one nonsteroidal antiinflammatory drug, selective COX-2 inhibitor, antacid, bismuth-containing reagent, acid-degradable antibacterial compound, and mixtures thereof. The present invention also provides methods for treating and/or preventing gastrointestinal disorders; facilitating ulcer healing; decreasing the recurrence of ulcers; improving gastroprotective properties, anti-*Helicobacter pylori* properties or antacid properties of proton pump inhibitors; decreasing or reducing the gastrointestinal toxicity associated with the use of nonsteroidal antiinflammatory compounds; treating *Helicobacter pylori* and viral infections. The compounds and/or compositions of the present invention can also be provided in the form of a pharmaceutical kit.

BACKGROUND OF THE INVENTION

The proton pump, located in the apical membrane of the parietal cell, is responsible for the secretion of acid in the stomach when it is stimulated by the enzyme adenosine triphosphate ($H^+$, $K^+$)-ATPase. Proton pump inhibitors are a class of anti-secretory compounds used in the management of gastrointestinal disorders. They suppress gastric acid secretion by the specific inhibition of the ($H^+$, $K^+$)-ATPase enzyme system at the secretory surface of the gastric parietal cell.

A family of substituted benzimidazoles have been developed as specific proton pump inhibitors. Two of these compounds, omeprazole and lansoprazole, are used clinically in the United States. Structurally they contain a sulfinyl group bridging between substituted benzimidazole and pyridine rings. At a neutral pH, omeprazole and lansoprazole are chemically stable, are weak bases, are lipid-soluble, and do not show any inhibitory activity. Once these compounds reach the parietal cells and diffuse into the secretory canaliculi, they become protonated. The protonated compounds rearrange to form sulfenic acid and then a sulfenamide. The latter interacts covalently with sulfhydryl groups at critical sites in the extracellular (luminal) domain of the membrane spanning ($H^+$, $K^+$)-ATPase. Inhibition occurs when two molecules of the inhibitor are bound per molecule of the enzyme. The specificity of these proton pump inhibitors arises from the selective distribution of the ($H^+$, $K^+$)-ATPase, the acid-catalyzed rearrangement of the compounds to generate the active inhibitor, and the trapping of the protonated compound and the cationic sulfenamide within the acidic canaliculi and adjacent to the target enzyme.

Omeprazole and lansoprazole are typically administered orally as delay-release capsules. The compounds are stable at a neutral pH, but are destroyed by gastric acid. Therefore, if the integrity of the gelatin-coated capsule is destroyed in any way and the patient swallows the enteric-coated grains, the neutral pH in the mouth and the esophagus will break down the microencapsulation, and the compounds will be degraded by the gastric acid in the stomach. The delay release: capsules, when appropriately taken, release the omeprazole and lansoprazole after the granules leave the stomach.

Despite their good anti-secretory properties, proton pump inhibitors are not unanimously recognized as gastroprotective agents. In addition, there is a high relapse rate associated with treating gastrointestinal disorders with proton pump inhibitors as they do not eliminate *Helicobacter pylori* (*Campylobacter pylori*), the bacteria responsible for peptic ulcer disease, gastric lymphoma and adenocarcinoma. U.S. Pat. Nos. 5,599,794 and 5,629,305 describe the administration of proton pump inhibitors in combination with acid-degradable antibacterial compounds for the treatment of infections caused by *Helicobacter pylori*.

A variety of adverse reactions have been ascribed to proton pump inhibitors, such as omeprazole and lansoprazole, reflecting, in part, the very large number of patients who have been treated with these drugs. The incidence of adverse reactions is low, and the adverse reactions are generally minor. Due to the profound reduction in gastric acidity, there tends to be an increased secretion of gastrin. Hence, patients who take therapeutic doses of omeprazole and lansoprazole have modest hypergastrinemia. Prolonged administration of high doses of the drugs can cause hyperplasia of oxyntic mucosal cells.

The most common side effects of proton pump inhibitors, such as omeprazole and lansoprazole, are nausea, diarrhea, abdominal colic, and central nervous system effects such as headaches and dizziness. Occasionally skin rashes and transient elevations of plasma activities of hepatic aminotransferase have been reported. The drugs can also result in bacterial overgrowth in the gastrointestinal tract and the development of nosocomial pneumonia.

There is a need in the art for proton pump inhibitors that have improved gastroprotective properties, decrease the recurrence of ulcers, facilitate ulcer healing and that can be used at low dosages. The present invention is directed to these, as well as other, important ends.

SUMMARY OF THE INVENTION

The present invention provides proton pump inhibitors to which is linked at least one NO and/or $NO_2$ group (i.e., nitrosylated and/or nitrosated). The proton pump inhibitors can be, for example, substituted benzimidazoles and substituted azabenzimidazoles, including, for example, omeprazole, pantoprazole, rabeprazole, leminoprazole, lansoprazole, timoprazole, tenatoprazole, disulprazole, esomeprazole, RO 18-5362 and IY 81149. The present invention also provides compositions comprising such compounds in a pharmaceutically acceptable carrier.

Another aspect of the invention provides compositions comprising at least one proton pump inhibitor, that is optionally substituted with at least one NO and/or $NO_2$ group (i.e., nitrosylated and/or nitrosated), and at least one compound that donates, transfers or releases nitric oxide and/or stimulates endogenous production of nitric oxide (NO) or endothelium-derived relaxing factor (EDRF) in vivo and/or is a substrate for nitric oxide synthase. The present invention also provides compositions comprising such compounds in a pharmaceutically acceptable carrier.

Yet another aspect of the present invention provides methods for treating gastrointestinal disorders, methods for improving the gastroprotective properties, anti-*Helicobacter* properties and antacid properties of proton pump inhibitors, methods for facilitating ulcer healing and methods for decreasing the rate of recurrence of ulcers in a patient in need thereof comprising administering to the patient at least one proton pump inhibitor that is substituted with at least one NO and/or $NO_2$ group, or by administering to the patient at least one proton pump inhibitor, that is optionally substituted with at least one NO and/or $NO_2$ group, and at least one compound that donates, transfers or releases nitric oxide and/or stimulates endogenous production of nitric oxide or EDRF in vivo. The proton pump inhibitor, that is optionally substituted with at least one NO and/or $NO_2$ group, and nitric oxide donor can be administered separately or as components of the same composition in one or more pharmaceutically acceptable carriers.

The present invention also provides methods to decrease or reverse gastrointestinal toxicity resulting from the administration of nonsteroidal antiinflammatory drugs (NSAIDs) and/or selective COX-2 inhibitors, and methods to facilitate ulcer healing resulting from the administration of NSAIDs and/or selective COX-2 inhibitors, in a patient in need thereof by administering the compounds and/or compositions of the present invention. The present invention also provides methods to treat infections caused by *Helicobacter pylori* and/or viruses in patients in need thereof by administering the compounds and/or compositions of the present invention.

These and other aspects of the present invention are described in detail herein.

DETAILED DESCRIPTION OF THE INVENTION

Figure 1:
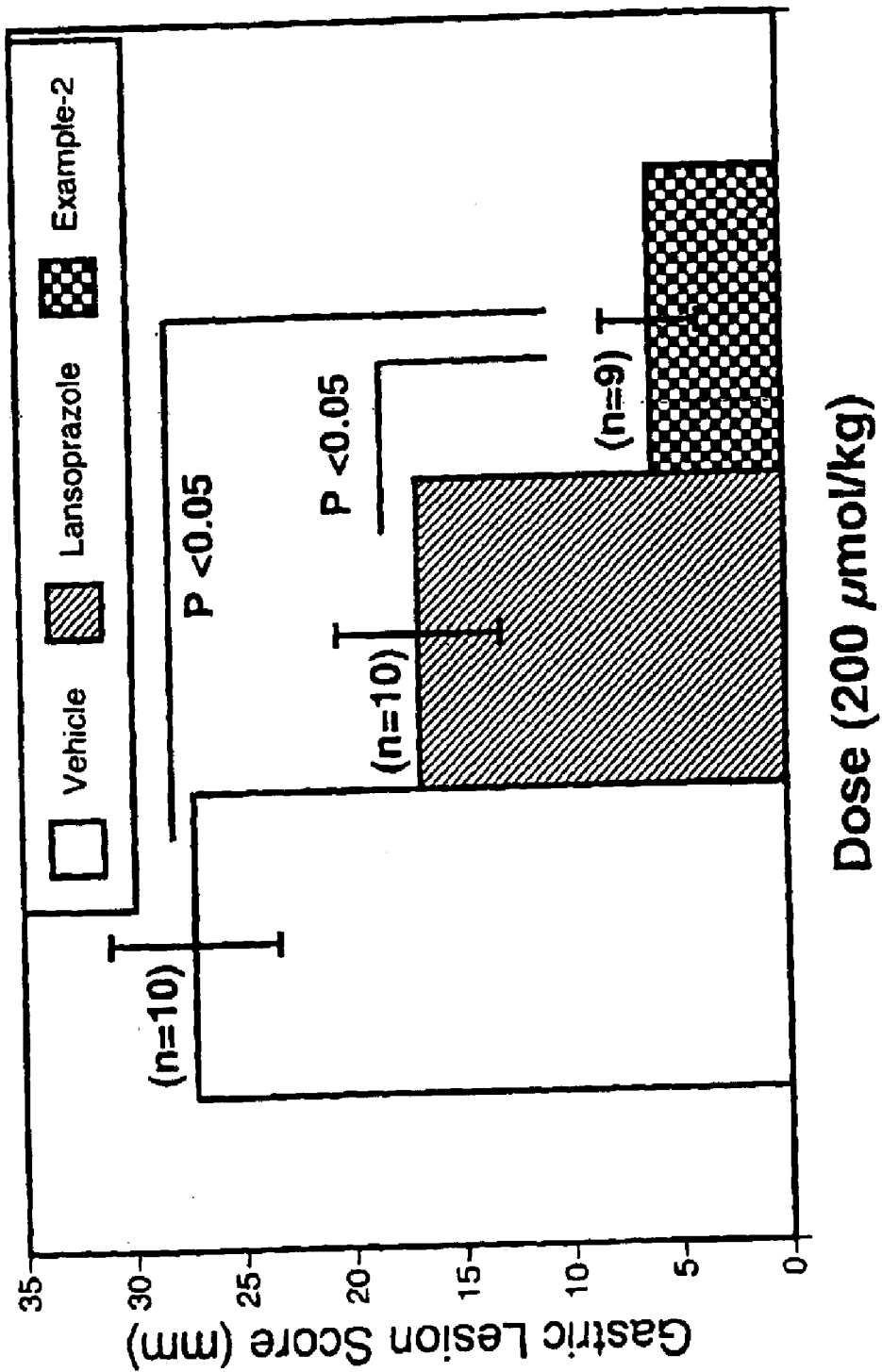
FIG. 1 shows the gastric lesion scores of (a) vehicle alone (open bar, n=10); (b) lanzoprazole in vehicle (stripped bar, n=10); and (c) example 2 (nitrosylated lanzoprazole) in vehicle (checked bar, n=9). Lanzoprazole at 200 μmol/kg did not significantly inhibit the formation of gastric lesions relative to vehicle alone. Example 2 (nitrosylated lanzoprazole) at 200 μmol/kg inhibited the formation of gastric lesions relative to vehicle alone (p<0.05) and lanzoprazole (p<0.05).

As used throughout the disclosure, the following terms, unless otherwise indicated, shall be understood to have the following meanings.

"Gastrointestinal disorder" refers to any disease or disorder of the upper and lower gastrointestinal tract of a patient including, for example, inflammatory bowel disease, Crohn's disease, irritable bowel syndrome, ulcerative colitis, peptic ulcers, stress ulcers, bleeding peptic ulcers, duodenal ulcers, infectious enteritis, colitis, diverticulitis, gastric hyperacidity, dyspepsia, gastroparesis, Zollinger-Ellison syndrome, gastroesophageal reflux disease, *Helicobacter Pylori* associated disease, short-bowel (anastomosis) syndrome, hypersecretory states associated with systemic mastocytosis or basophilic leukemia and hyperhistaminemia that result, for example, from neurosurgery, head injury, severe body trauma or burns.

"Upper gastrointestinal tract" refers to the esophagus, the stomach, the duodenum and the jejunum.

"Lower gastrointestinal tract" refers to the ileum, the colon, the cecum and the rectum.

"Ulcers" refers to lesions of the upper gastrointestinal tract lining that are characterized by loss of tissue. Such ulcers include gastric ulcers, duodenal ulcers and gastritis.

"Viral infection" refers to both RNA and DNA viral infections. The RNA viral infections include, but are not limited to, orthomyxoviridae, paramyxoviridae, picornaviridae, rhabdoviridae, coronavaridae, togaviridae, bunyaviridae, arenaviridae and reteroviridae. The DNA viral infections include, but are not limited to, adenoviridae, proxyiridae, papovaviridae, herpetoviridae and herpesviridae. The most preferable viral infections are those of the herpetoviridae family, such as, for example, herpes simplex viruses HSV-1 and HSV-2, cytomegalovirus (CMV), herpes varicella-zoster (VZV), Epstein-Barr (EBV), HHV6, HHV7, pseudorabies and rhinotracheitis, and the like.

"Proton pump inhibitor" refers to any compound that reversibly or irreversibly blocks gastric acid secretion by inhibiting the $H^+/K^+$-ATP ase enzyme system at the secretory surface of the gastric parietal cell.

"NSAID" refers to a nonsteroidal anti-inflammatory compound or a nonsteroidal anti-inflammatory drug. NSAIDs inhibit cyclooxygenase, the enzyme responsible for the biosyntheses of the prostaglandins and certain autocoid inhibitors, including inhibitors of the various isozymes of cyclooxygenase. (including but not limited to cyclooxygenase-1 and -2), and as inhibitors of both cyclooxygenase and lipoxygenase.

"Cyclooxygenase-2 (COX-2) inhibitor" refers to a compound that selectively inhibits the cyclooxygenase-2 enzyme over the cyclooxygenase-1 enzyme. Preferably, the compound has a cyclooxygenase-2 $IC_{50}$ of less than about 0.5 μM, and also has a selectivity ratio of cyclooxygenase-2 inhibition over cyclooxygenase-1 inhibition of at least 50, and more preferably of at least 100. Even more preferably, the compound has a cyclooxygenase-1 $IC_{50}$ of greater than about 1 μM, and more preferably of greater than 20 μM. The compound can also inhibit the enzyme, lipoxygenase.

"Patient" refers to animals, preferably mammals, more preferably humans.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, NO.), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO^-$, NO.), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium derived relaxing factor (EDRF) in vivo and/or elevate endogenous levels of nitric oxide or EDRF in vivo. "NO donor" also includes compounds that are substrates for nitric oxide synthase.

"Alkyl" refers to a lower alkyl group, a haloalkyl group, an alkenyl group, an alkynyl group, a bridged cycloalkyl group, a cycloalkyl group or a heterocyclic ring, as defined herein.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, isoamyl, hexyl, octyl, and the like.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon—carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Alkynyl" refers to an unsaturated acyclic $C_2$-Cl, hydrocarbon (preferably a $C_2$–$C_6$ hydrocarbon, more preferably a $C_2$–$C_6$ hydrocarbon) which can comprise one or more carbon—carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more cycloalkyl groups, heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo[3.3.0] octane, 7-oxabycyclo[2.2.1]heptyl, 8-azabicyclo[3,2,1]oct-2-enyl and the like.

"Cycloalkyl" refers to a saturated or unsaturated cyclic hydrocarbon comprising from about 3 to about 8 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo and nitro. Exemplary cycloalkyl groups include cyclopropyl, cyclobutyl, cyclopentyl, cyclohexyl, cyclohexenyl, cyclohepta,1,3-dienyl, and the like.

"Heterocyclic ring or group" refers to a saturated, unsaturated cyclic or polycyclic hydrocarbon group having about 3 to about 12 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylamino, dialkylamino, arylamino, diarylamino, alkylarylamino, hydroxy, oxo, thial, halo, carboxyl, carboxylic ester, alkylcarboxylic acid, alkylcarboxylic ester, aryl, arylcarboxylic acid, arylcarboxylic ester, amidyl, ester, carboxamido, alkylcarboxamido, arylcarboxamido, sulfonic acid, sulfonic ester, sulfonamido and nitro. Exemplary heterocyclic groups include pyrrolyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, 2-pyrrolinyl, 3-pyrrolinyl, pyrrolindinyl, oxazolindinyl 1,3-dioxolanyl, 2,6-dioxabicyclo[3,3,0]octanyl, 2-imidazonlinyl, imidazolindinyl, 2-pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicylic aryl groups) can be unsubstituted or substituted with one, two or three substituents independently selected from alkyl, alkoxy, amino, alkylamino, dialkylamino, arylamino, diarylamino, alkylarylamino, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl; ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkyl" refers to an aryl radical, as defined herein, attached to an alkyl radical, as defined herein.

"Cycloalkylalkyl" refers to a cycloalkyl radical, as defined herein, attached to an alkyl radical, as defined herein.

"Heterocyclicalkyl" refers to a heterocyclic ring radical, as defined herein, attached to an alkyl radical, as defined herein.

"Cycloalkenyl" refers to an unsaturated cyclic hydrocarbon having about 3 to about 10 carbon atoms (preferably about 3 to about 8 carbon atoms, more preferably about 3 to about 6 carbon atoms) comprising one or more carbon—carbon double bonds.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O—$, wherein $R_{50}$ is an alkyl group, as defined herein. Exemplary alkoxy groups include methoxy, ethoxy, t-butoxy, cyclopentyloxy, and the like.

"Arylalkoxy or alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O—$, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Haloalkoxy" refers to a haloalkyl group, as defined herein, to which is appended an alkoxy group, as defined herein. Exemplary haloalkyl groups include 1,1,1-trichloroethoxy, 2-bromobutoxy, and the like.

"Hydroxy" refers to —OH.

"Oxo" refers to =O.

"Oxy" refers to $—O^-R_{77}^+$ wherein $R_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Amino" refers to $—NH_2$.

"Nitrate" refers to $—O—NO_2$.

"Nitrite" refers to —O—NO.

"Thionitrate" refers to $—S—NO_2$.

"Thionitrite" and "nitrosothiol" refer to —S—NO.

"Nitro" refers to the group $—NO_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Alkylamino" refers to $R_{50}NH—$, wherein $R_{50}$ is an alkyl group, as defined herein. Exemplary alkylamino groups include methylamino, ethylamino, butylamino, cyclohexylamino, and the like.

"Arylamino" refers to $R_{55}NH—$, wherein $R_{55}$ is an aryl group, as defined herein.

"Dialkylamino" refers to $R_{50}R_{52}N—$, wherein $R_{50}$ and $R_{52}$ are each independently an alkyl group, as defined herein. Exemplary dialkylamino groups include dimethylamino, diethylamino, methyl propargylamino, and the like.

"Diarylamino" refers to $R_{55}R_{60}N—$, wherein $R_{50}$ and $R_{60}$ are each independently an aryl group, as defined herein.

"Alkylarylamino" refers to $R_{50}R_{60}N—$, wherein $R_{50}$ is an alkyl group, as defined herein, and $R_{55}$ is an aryl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein.

"Aminoaryl" refers to an amino group, an alkylamino group, a dialkylamino group, an arylamino group, a diarylamino group, an alkylarylamino group or a heterocyclic ring, as defined herein, to which is appended an aryl group, as defined herein.

"Thio" refers to —S—.

"Sulfinyl" refers to —S(O)—.

"Methanthial" refers to —C(S)—.

"Thial" refers to =S.

"Sulfonyl" refers to $—S(O)_2$.

"Sulfonic acid" refers to $—S(O)_2OR_{76}$, wherein $R_{76}$ is a hydrogen, an organic cation or an inorganic cation.

"Alkylsulfonic acid" refers to a sulfonic acid group, as defined herein, appended to an alkyl group, as defined herein.

"Arylsulfonic acid" refers to an sulfonic acid group, as defined herein, appended to an aryl group, as defined herein.

"Sulfonic ester" refers to $—S(O)_2OR_{58}$, wherein $R_{58}$ is an alkyl group, an aryl group, an alkylaryl group or an aryl heterocyclic ring, as defined herein.

"Sulfonamido" refers to $—S(O)_2—N(R_{51})(R_{57})$, wherein $R_{51}$ and $R_{57}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Sulfamoyl" refers to $R_{51}S(O)_2—N(R_{57})—$, wherein $R_{51}$, and $R_{57}$ are each independently a hydrogen atom, an alkyl group, an aryl group, an alkylaryl group, or an arylheterocyclic ring, as defined herein, and $R_{51}$ and $R_{57}$ when taken together are a heterocyclic ring, a cycloalkyl group or a bridged cycloalkyl group, as defined herein.

"Alkylthio" refers to $R_{50}S—$, wherein $R_{50}$ is an alkyl group, as defined herein.

"Arylthio" refers to $R_{55}S—$, wherein $R_{55}$ is an aryl group, as defined herein.

"Cycloalkylthio" refers to $R_{54}S—$, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Alkylsulfinyl" refers to $R_{50}—S(O)—$, wherein $R_{50}$ is an alkyl group, as defined herein.

"Alkylsulfonyl" refers to $R_{50}—S(O)_2—$, wherein $R_{50}$ is an alkyl group, as defined herein.

"Arylsulfinyl" refers to $R_{55}—S(O)—$, wherein $R_{55}$ is an aryl group, as defined herein.

"Arylsulfonyl" refers to $R_{55}—S(O)_2—$, wherein $R_{55}$ is an aryl group, as defined herein.

"Amidyl" refers to $R_{51}C(O)N(R_{57})—$ wherein $R_{51}$ and $R_{57}$ are each independently a hydrogen atom, an alkyl group, an aryl group, an alkylaryl group, or an arylheterocyclic ring, as defined herein.

"Ester" refers to $R_{51}C(O)O$— wherein $R_{51}$ is a hydrogen atom, an alkyl group, an aryl group, an alkylaryl group, or an arylheterocyclic ring, as defined herein.

"Carbamoyl" refers to $—O—C(O)N(R_{51})(R_{57})$, wherein $R_{51}$ and $R_{57}$ are each independently a hydrogen atom, an alkyl group, an aryl group, an alkylaryl group or an arylheterocyclic ring, as defined herein, or $R_{51}$ and $R_{57}$ taken together are a heterocyclic ring, a cycloalkyl group or a bridged cycloalkyl group, as defined herein.

"Carboxyl" refers to $—C(O)OR_{76}$, wherein $R_{76}$ is a hydrogen, an organic cation or an inorganic cation, as defined herein.

"Carbonyl" refers to $—C(O)—$.

"Alkylcarbonyl" or "alkanoyl" refers to $R_{50}—C(O)—$, wherein $R_{50}$ is an alkyl group, as defined herein.

"Arylcarbonyl" or "aroyl" refers to $R_{55}—C(O)—$, wherein $R_{55}$ is an aryl group, as defined herein.

"Carboxylic ester" refers to $—C(O)OR_{58}$, wherein $R_{58}$ is an alkyl group, an aryl group, an alkylaryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to $—C(O)N(R_{51})(R_{57})$, wherein $R_{51}$ and $R_{57}$ are each independently a hydrogen atom, an alkyl group, an aryl group, an alkylaryl group or an arylheterocyclic ring, as defined herein, and $R_{51}$ and $R_{57}$ when taken together are a heterocyclic ring, a cycloalkyl group or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Urea" refers to $—N(R_{59})—C(O)N(R_{51})(R_{57})$ wherein $R_{51}$, $R_{57}$, and $R_{59}$ are each independently a hydrogen atom, an alkyl group, an aryl group, an alkylaryl group, or an arylheterocyclic ring, as defined herein, or $R_{51}$ and $R_{57}$ taken together are a heterocyclic ring, a cycloalkyl group or a bridged cycloalkyl group, as defined herein.

"Phosphoryl" refers to $—P(R_{70})(R_{71})(R_{72})$, wherein $R_{70}$ is a lone pair of electrons, sulfur or oxygen, and $R_{71}$ and $R_{72}$ are each independently a covalent bond, a hydrogen, a lower alkyl, an alkoxy, an alkylamino, a hydroxy or an aryl, as defined herein.

Compounds that donate, transfer or release nitric oxide species in vivo have a wide spectrum of advantages and applications. The present invention is based on the discovery of the effects of such compounds together with one or more proton pump inhibitors and/or one or more proton pump inhibitors directly or indirectly linked with one or more nitric oxide moieties. Treatment or prevention of gastrointestinal disorders, improved gastroprotective properties, decreased rate of recurrence of peptic ulcers and faster ulcer healing can be obtained by the use of the nitrosated and/or nitrosylated proton pump inhibitors of the present invention. Treatment or prevention of gastrointestinal disorders, improved gastroprotective properties, decreased rate of recurrence of peptic ulcers and faster ulcer healing can also be obtained by the use of one or more proton pump inhibitors, that are optionally directly or indirectly linked with one or more nitric oxide moieties, in conjunction with one or more compounds that donate, release or transfer nitric oxide or stimulate endogenous production of nitric oxide or EDRF in vivo or are substrates for nitric oxide synthase.

Proton pump inhibitors are compounds that selectively inhibit gastric acid secretion by the specific inhibition of the $(H^+, K^+)$-ATPase enzyme system at the secretory surface of the gastric parietal cell. A nitric oxide donor is a compound that contains at least one nitric oxide adduct and releases or chemically transfers a biologically active nitrogen monoxide species.

The compounds and compositions of the present invention are novel and can be used to treat numerous gastrointestinal diseases and disorders. Such gastrointestinal disorders include, for example, inflammatory bowel disease, Crohn's disease, irritable bowel syndrome, ulcerative colitis, peptic ulcers, stress ulcers, bleeding peptic ulcers, duodenal ulcers, infectious enteritis, colitis, diverticulitis, gastric hyperacidity, gastric hyperacidity, dyspepsia, gastroparesis, Zollinger-Ellison syndrome, gastroesophageal reflux disease, *Helicobacter Pylori* associated disease, short-bowel (anastomosis) syndrome, hypersecretory states associated with systemic mastocytosis or basophilic leukemia and hyperhistaminemia that result, for example, from neurosurgery, head injury, severe body trauma or burns. The compounds and compositions of the present invention can also be used as a pre-anesthetic medication in emergency operations to reduce the danger of aspiration of acidic gastric contents.

The proton pump inhibitors used in the compounds and compositions of the present invention can be any of those known in the art, such as those exemplified herein.

Omeprazole, i.e., 5-methoxy-2((4-methoxy-3,5-dimethyl-2-pyridinyl)methyl)-sulfinyl)-1H-benzimidazole, (marketed under the trade name PRILOSEC® by Astra Merck, Wayne, Pa.) and lansoprazole, i.e., 2-(((3-methyl-4-(2,2,2-trifluoro-ethoxy)-2-pyridinyl)methyl)sulfinyl)-1H-benzimidazole (marketed under the trade name PREVACID® by TAP Pharmaceutical Inc., Deerfield, Ill.) are two of the most widely used compounds that inhibit gastric acid secretion. Other useful compounds include rabeprazole, i.e., 2-(((4-(3-methoxypropoxy)-3-methyl-2-pyridinyl)methyl)sulfinyl)-1H-benzimidazole (marketed under the trade name ACIPHEX® by Eisai, Inc.), pantoprazole, i.e., 5-(difluoromethoxy)-2-(((3,4-dimethoxy-2-pyridinyl) methyl)sulfinyl)-1H-benzimidazole, leminoprazole, timoprazole, tenatoprazole, disulprazole, esomeprazole, RO 18-5362, IY 81149. These compound do not exhibit anticholinergic or histamine $H_2$-receptor antagonist properties, but suppress gastric acid secretion by the specific inhibition of $(H^+, K^+)$-ATPase enzyme system at the secretory surface of the gastric parietal cell. As this enzyme system is regarded as the acid (proton) pump within the parietal cell, these substituted benzimidazoles have been characterized as gastric-acid-pump inhibitors as they block the final step of acid production. Although the proton pump inhibitor antisecretory agents are effective in treating gastrointestinal disorders, they do not have any gastroprotective properties and, in addition, there is a high recurrence of ulcers associated with their use.

Another group of proton pump inhibitors are substituted quinolines, which include, for example, 3-butyl-4-(2-methylphenylamino)-8-(2-hydroxyethoxy)-quinoline.

Other proton pump inhibitors are disclosed in, for example, U.S. Pat. Nos. 4,045,564, 4,255,431, 4,634,710, 4,758,579, 4,806,549,4,806,550, 4,818,760, 4,839,365, 4,845,118, 4,871,734, 4,873,337, 4,956,366, 4,981,861, 5,114,955, 5,149,702, 5,439,917, 5,554,631, 5,665,730, 5,677,302, 5,686,458, 5,703,097, 5,750,531, 5,990,311, 5,952,504 and 5,945,425 and in EP 0 033 094 B1, EP 0 045 200 A1, EP 0 221 041 A2, EP 0 234 485 A1, EP 0 246 774 A1, EP 0 254 588 A1, EP 0 259 174 A1 and in WO 89/08104, WO 92/12969, WO 95/27714, WO 97/32854, WO 98/18784, WO 98/43968, WO 98/54172; the disclosures of each of which are incorporated by reference herein in their entirety.

Several of the above contemplated proton pump inhibitors are described more fully in the literature, such as in Goodman and Gilman, The Pharmacological Basis of Therapeutics (9th Edition), McGraw-Hill, pages 901–915 (1996); Merck Index on CD-ROM, Twelfth Edition, Version 12:1, (1996); STN Express, file phar and file registry, the disclosures of which are incorporated by reference herein in their entirety.

The proton pump inhibitors of the present invention can be nitrosated and/or nitrosylated through one or more sites such as oxygen (hydroxyl condensation), sulfur (sulfhydryl condensation), carbon and nitrogen. The proton pump inhibitor compounds that are nitrosated and/or nitrosylated in accordance with the invention and/or are included in the compositions of the invention can be any of those known in the art, including those exemplified below.

In one embodiment, the present invention describes nitrosated and/or nitrosylated proton pump inhibitors of Formula (I) or a pharmaceutically acceptable salt thereof:

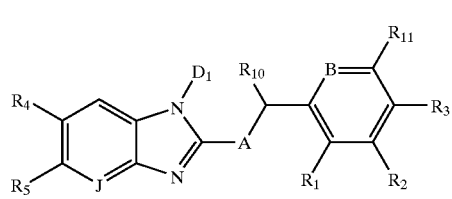

(I)

wherein
A is S, S(O), or S(O)$_2$;
B is —CNR$_7$R$_7$' or nitrogen;
J is CH or nitrogen;
R$_1$ is a hydrogen, an alkoxy group, a lower alkyl group, or an alkylthio group;
R$_2$ is a hydrogen, an alkoxy group, a lower alkyl group, an alkylthio group, a haloalkoxy group, an alkoxyalkyl group, —NR$_7$R$_7$', —OD$_1$, or —SD$_1$; or R$_2$ and R$_1$ taken together with the carbon chain to which they are attached form a cycloalkyl ring or a heterocyclic ring; or R$_2$ and R$_3$ taken together with the carbon chain to which they are attached form a cycloalkyl ring or a heterocyclic ring;
R$_3$ and R$_{11}$ are each independently a hydrogen, an alkoxy group, a lower alkyl group, or an alkylthio group; or R$_3$ and R$_{11}$ taken together with the carbon chain to which they are attached form a cycloalkyl ring or a heterocyclic ring;
R$_4$ and R$_5$ are each independently a hydrogen, an alkyl group, a halo group, an alkoxy group, a haloalkyl group, a haloalkoxy group, a cyano group, an aryl group, a heterocyclic ring, —NR$_7$R$_7$', —OD$_1$, or —CO$_2$R$_{12}$; or R$_4$ and R$_5$ taken together are:

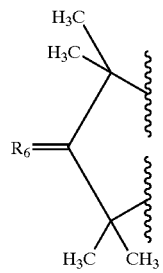

wherein
R$_6$ is oxygen or N=O—R$_7$;
R$_7$ and R$_7$' are each independently hydrogen, a lower alkyl group or D; or R$_7$ and R$_7$' taken together with the nitrogen to which they are attached form a heterocyclic ring;
R$_{10}$ is a hydrogen; or R$_{10}$ and R$_1$ taken together with the carbon chain to which they are attached form a cycloalkyl ring;
R$_{12}$ is a lower alkyl group or D;
D$_1$ is a hydrogen or D;
D is Q or K;
Q is —NO or —NO$_2$;
K is —W$_a$—E$_b$—(C(R$_e$)(R$_f$))$_p$—E$_c$—(C(R$_e$)(R$_f$))$_x$—W$_d$—(C(R$_e$)(R$_f$))$_y$—W$_i$—E$_j$—W$_g$—(C(R$_e$)(R$_f$))$_z$—T—Q;
a, b, c, d, g, i and j are each independently an integer from 0 to 3;
p, x, y and z are each independently an integer from 0 to 10;
W at each occurrence is independently (O), —C(S)—, —T—, —(C(R$_e$)(R$_f$))$_h$—, an alkyl group, an aryl group, a heterocyclic ring, an arylheterocyclic ring, or —(CH$_2$CH$_2$O)$_q$—;
E at each occurrence is independently —T—, an alkyl group, an aryl group, —(C(R$_e$)(R$_f$))$_h$—, a heterocyclic ring, an arylheterocyclic ring, or —(CH$_2$CH$_2$O)$_q$—;
h is an integer form 1 to 10;
q is an integer from 1 to 5;
R$_e$ and R$_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or (C(R$_e$)(R$_f$))$_k$—T—Q, or R$_e$ and R$_f$ taken together with the carbons to which they are attached form a carbonyl, a methanthial, a heterocyclic ring, a cycloalkyl group or a bridged cycloalkyl group;
k is an integer from 1 to 3;

T at each occurrence is independently a covalent bond, a carbonyl, an oxygen, —S(O)$_o$— or —N(R$_a$)R$_i$—;

o is an integer from 0 to 2;

R$_a$ is a lone pair of electrons, a hydrogen or an alkyl group;

R$_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T—Q)(R$_e$)(R$_f$), or —(N$_2$O$_2$—)$_-$.M$^+$, wherein M$^+$ is an organic or inorganic cation; with the proviso that when R$_i$ is CH$_2$—C(T—Q)(R$_e$)(R$_f$) or —(N$_2$O$_2$)$^-$ .M$^+$, or R$_e$ or R$_f$ are T—Q or (C(R$_e$)(R$_f$))$_k$—T—Q, then the "—T—Q" subgroup can be a hydrogen, an alkyl, an alkoxy, an alkoxyalkyl, an aminoalkyl, a hydroxy, a heterocyclic ring or an aryl group; and with the proviso that the compounds of Formula (I) must contain at least one nitrite, nitrate, thionitrite or thionitrate group.

In cases where R$_e$ and R$_f$ are a heterocyclic ring or taken together R$_e$ and R$_f$ are a heterocyclic ring, then R$_i$ can be a substituent on any disubstituted nitrogen contained within the radical where R$_i$ is as defined herein.

In cases where multiple designations of variables which reside in sequence are chosen as a "covalent bond" or the integer chosen is 0, the intent is to denote a single covalent bond connecting one radical to another. For example, E$_0$ would denote a covalent bond, while E$_2$ denotes (E—E) and (C(R$_a$)(R$_i$))$_2$ denotes —C(R$_e$)(R$_f$)—C(R$_e$)(R$_f$)—.

Another embodiment of the present invention describes compounds of Formula (II) or pharmaceutically acceptable salts thereof:

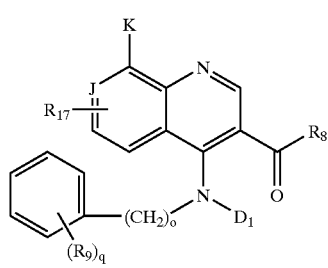

II wherein

R$_8$ is a lower alkyl group, an alkoxyalkyl group, an alkylaryl group, a cycloalkyl group, a cycloalkylalkyl group, an aryl group, an alkylaryl group, or K;

R$_9$ at each occurrence is independently a hydrogen, a lower alkyl group, an alkylthio group, a halogen, a cyano group an alkanoyl group, a haloalkyl group, a carbamoyl group, —NR$_7$D$_1$, —OD$_1$, or —CO$_2$R$_{12}$;

R$_{71}$ is a hydrogen, a lower alkyl group, an alkoxy group, or —OD$_1$;

J, K, D$_1$, R$_7$, R$_{12}$, q and o are as defined herein; and with the proviso that the compounds of Formula (II) must contain at least one nitrite, nitrate, thionitrite or thionitrate group.

Another embodiment of the present invention describes compounds of Formula (III) or pharmaceutically acceptable salts thereof:

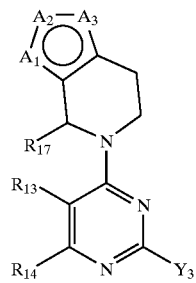

III wherein

R$_{13}$ and R$_{14}$ are each independently a hydrogen a lower alkyl group, an alkoxyalkyl, or a lower alkyl-OD$_1$; or R$_{13}$ and R$_{14}$ taken together along with the carbons to which they are attached form a cycloalkyl group or an aryl group;

R$_{17}$ is a hydrogen or a lower alkyl group;

Y$_3$ is:

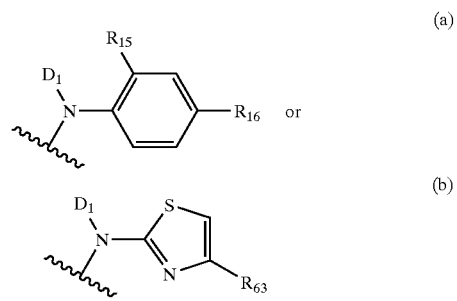

wherein

R$_{15}$ is a hydrogen or a lower alkyl group;

R$_{16}$ is a hydrogen, a halogen, or a lower alkyl group;

R$_{63}$ is a lower alkyl group or a phenyl group;

A$_1$, A$_2$ and A$_3$ comprise the other subunits of a 5- or 6-membered monocyclic aromatic ring and A$_1$, A$_2$ and A$_3$ are each independently:

(i) CR$_o$, wherein R$_o$ at each occurrence is hydrogen or —OD$_1$;

(ii) N—R$_p$, wherein R$_p$ at each occurrence is independently a covalent bond to an adjacent ring atom in order to render the ring aromatic, a hydrogen, or K;

(iii) a sulfur atom;

(iv) an oxygen atom; or (v) B$_a$=B$_b$, wherein B$_a$ and B$_b$ are each independently a nitrogen atom or CR$_o$; wherein R$_o$ at each occurrence is hydrogen or —OD$_1$;

D$_1$ and K are as defined herein; and with the proviso that the compounds of Formula (III) must contain at least one nitrite, nitrate, thionitrite or thionitrate group.

Another embodiment of the present invention describes compounds of Formula (IV) or pharmaceutically acceptable salts thereof:

IV

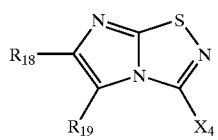

wherein $R_{18}$ and $R_{19}$ at each occurrence are each independently a hydrogen, a lower alkyl group, a halogen, a nitro group, an alkoxy group, —$OD_1$, —$NR_{20}R_{21}$, —$O(O)CR_{20}$, —$O(O)COR_{20}$, —$O(O)CNR_{20}R_{21}$, —$N(R_{20})C(O)R_{21}$, —$N(R_{20})C(O)NR_{20}R_{21}$, or —$N(R_{20})C(O)OR_{21}$; or $R_{18}$ and $R_{19}$ when taken together along with the carbons to which they are attached form a heterocyclic ring or a phenyl ring optionally substituted with up to four substituents selected from a hydrogen, a lower alkyl group, a halogen, a nitro group, an alkoxy group, —$OD_1$, —$NR_2OR_{21}$, —$O(O)CR_{20}$, —$O(O)COR_{20}$, —$O(O)CNR_{20}R_{21}$, —$N(R_{20})C(O)R_{21}$, —$N(R_{20})C(O)NR_{20}R_{21}$, or —$N(R_{20})C(O)OR_{21}$;

$R_{20}$ and $R_{21}$ at each occurrence are each independently a hydrogen, a lower alkyl group, an aryl group, a lower alkylaryl group, or K;

$X_4$ is —$C(=R_6)R_{22}$, a heterocyclic ring, —$NR_{20}R_{21}$, a halogen, an alkoxy group, an arylalkoxy group, a cycloalkoxy group, a heterocyclicalkoxy group, an alkylsulfonyl group, an alkylsulfinyl group, an arylsulfonyl group, an arylsulfinyl group an arylalkylsulfonyl group, an arylalkylsulfinyl group, a heterocyclicsulfonyl group, or a heterocyclicsulfinyl group;

$R_{22}$ is a hydrogen, an alkyl group, an alkoxy group, an aryl group, an alkylaryl group, a heterocyclic ring, an —O-heterocyclic ring, or an alkylheterocyclic ring;

$D_1$, $R_6$, and K are defined as herein; and with the proviso that the compounds of Formula (IV) must contain at least one nitrite, nitrate, thionitrite or thionitrate group.

Another embodiment of the present invention describes compounds of Formula (V) or pharmaceutically acceptable salt thereof:

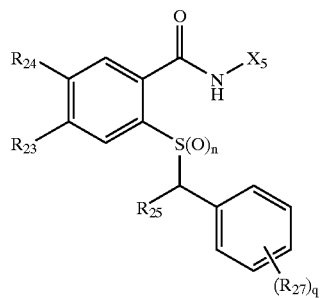

(V)

wherein
$X_5$ is:

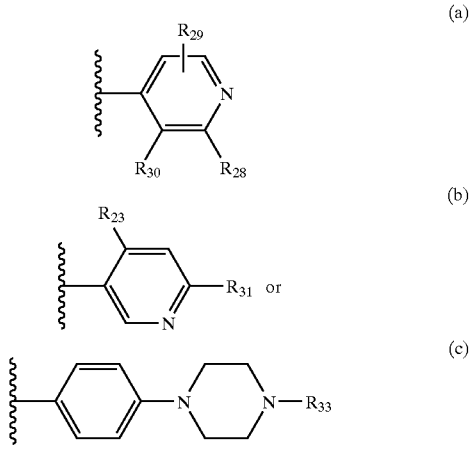

wherein
$R_{23}$ is a hydrogen, a dialkylamino group, —$NR_7R_7'$, or a heterocyclic ring;

$R_{24}$ is a hydrogen or halogen;

$R_{25}$ is a hydrogen, —$OD_1$, or lower alkyl-$OD_1$;

$R_{27}$ at each occurrence is independently a hydrogen or an alkoxy group;

$R_{28}$, $R_{29}$, and $R_{30}$ are each independently a hydrogen, a lower alkyl group, a dialkylamino group, a heterocyclic ring, or a lower alkyl-$OD_1$;

$R_{31}$ is a hydrogen, a dialkylamino group, or an alkoxy group;

$R_{33}$ is a hydrogen or a lower alkyl group;

n is an integer from 0 to 1;

$R_7$, $R_7'$, $D_1$ and q are as defined herein; and with the proviso that the compounds of Formula (V) must contain at least one nitrite, nitrate, thionitrite or thionitrate group.

Another embodiment of the present invention describes compounds of Formula (VI) or pharmaceutically acceptable salts thereof:

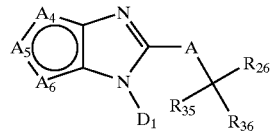

VI wherein
$A_4$, $A_5$, and $A_6$ are each independently a sulfur or $CR_{34}$ with the proviso that one of $A_4$, $A_5$, or $A_6$ is a sulfur and the other two are $CR_{34}$;

$R_{34}$ at each occurrence is independently a hydrogen, a halogen, a cyano, a nitro, a trifluoromethyl, a lower alkyl group, a heterocyclic ring, a lower alkyl-$OD_1$, an alkoxy, a haloalkoxy, an alkylthio, an alkylsulfinyl, an alkylsulfonyl, an alkylcarbonyl, an alkoxycarbonyl, a carbamoyl, a N-alkylcarbamoyl, a N,N-dialkylcarbamoyl, an ester, a cycloalkyl, an aryl, an alkylaryl, an aryloxy, an arylalkoxyoxy, an arylamino, a alkylarylamino, an arylthio, an arylsulfonyl, an arylsulfinyl, or a sulfonamido;

$R_{35}$ and $R_{36}$ are each independently a hydrogen or a lower alkyl group; or $R_{35}$ and $R_{41}$ taken together with the carbon chain to which they are attached form a cycloalkyl ring;

$R_{26}$ is:

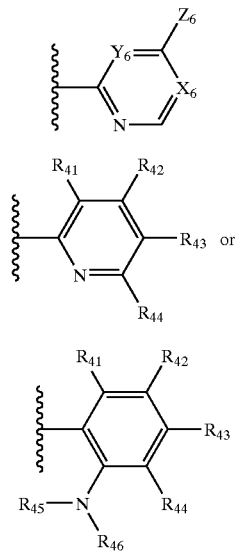

wherein $X_6$ is nitrogen, and $Y_6$ is $CR_{37}$; or $X_6$ is $CR_{37}$, and $Y_6$ is nitrogen;

$R_{37}$ is a hydrogen, a halogen, a lower alkyl group, a trifluoromethyl, an alkoxy group, a haloalkoxy group, an aryl group, an arylalkoxy group, a heterocyclic ring, or an aryloxy;

$Z_6$ is —$NR_{38}R_{39}$, $SR_{40}$, or an arylalkoxy group;

$R_{38}$ and $R_{39}$ are each independently a hydrogen, a lower alkyl group, an aryl group, an alkylaryl group, or a cycloalkyl group; or $R_{38}$ and $R_{39}$ taken together with the nitrogen to which they are attached form a heterocyclic ring;

$R_{40}$ is a hydrogen, a halogen, a lower alkyl group, an alkylaryl group, an alkenyl group, or a haloalkyl group;

$R_{41}$, $R_{42}$, $R_{43}$ and $R_{44}$ are each independently a hydrogen, a halogen, a lower alkyl group, an alkoxy group, a haloalkoxy group, an alkoxyaryl group, an alkylthio group, an alkysulfinyl group, an alkylsulfonyl group, a cyano group, —Y—$OD_1$, —Y—$SD_1$, —Y—$NR_{20}R_{21}$, —Y—O(O)$CR_{20}$, —Y—O(O)$CNR_{20}R_{21}$, —Y—N($R_{20}$)C(O)$R_{21}$, or —Y—N($R_{20}$)S(O)$_2R_{21}$;

Y is —$(CH_2)_a$— or a phenyl group;

$R_{45}$, and $R_{46}$ are each independently a hydrogen, a lower alkyl group, a cycloalkyl group, an alkenyl group, or an alkynyl group;

$D_1$, $R_{20}$, $R_{21}$, and a are as defined herein; and with the proviso that the compounds of Formula (VI) must contain at least one nitrite, nitrate, thionitrite or thionitrate group.

Another embodiment of the present invention describes compounds of Formula (VII) or pharmaceutically acceptable salts thereof:

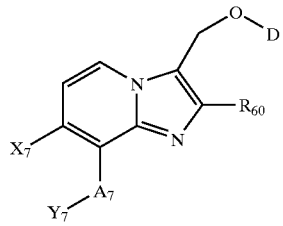

VII wherein $R_{60}$ is a lower alkyl group, an aryl group, a haloalkyl group, a lower alkyl-$OD_1$, or heterocyclic ring;

$A_7$ is oxygen or —$ND_1$;

$X_7$ is a hydrogen or a halogen;

$Y_7$ is:

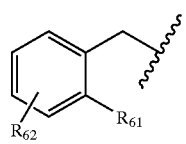

or $X_7$, $A_7$, and $Y_7$ taken together along with the carbons to which they are attached is:

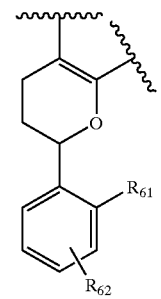

wherein $R_{61}$ is a hydrogen, a halogen, a lower alkyl group, —$OD_1$, or —NHC(O)O—lower alkyl;

$R_{62}$ is a hydrogen, a halogen, or a lower alkyl group; and $D_1$, is as defined herein.

Compounds of the present invention that have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof.

It is also to be understood that the present invention is intended to include within its scope compounds which may exist in more than one resonance form and the effects that the resonance form may have on the positions at $D_1$ substituents designated in the structures described herein.

Another embodiment of the present invention provides processes for making the novel compounds of the present invention and to the intermediates useful in such processes. The reactions are performed in solvents appropriate to the reagents and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of sulfur, oxygen and nitrogen-protecting groups is well known in the art for protecting thiol, alcohol, and amino groups against undesirable reactions during a synthetic procedure and many such protecting groups are known and described by, for example, Greene and Wuts, *Protective Groups in Organic Synthesis*, Third Edition, John Wiley & Sons, New York (1999).

The chemical reactions described herein are generally disclosed in terms of their broadest application to the preparation of the compounds of this invention. Occasionally, the reactions may not be applicable as described to each compound included within the disclosed scope. The compounds for which this occurs will be readily recognized by one skilled in the art. In all such cases, either the reactions can be successfully performed by conventional modifications known to one skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

The compounds of Formulas (I), (II), (III), (IV), (V), (VI) and (VII) can be synthesized by one skilled in the art following the methods and examples described herein. The synthesis of the parent proton pump inhibitors (i.e. non-nitrosated and non-nitrosylated proton pump inhibitors) are disclosed in, for example, U.S. Pat. Nos. 4,045,564, 4,255,431, 4,634,710, 4,758,579, 4,839,365, 4,873,337, 4,981,861, 5,149,702, 5,554,631, 5,703,097 and 5,945,425 and in EP 0 045 200 A1, EP 0 221 041 A2, EP 0 246 774 A1 and EP 0 254 588 A1 and in WO 98/54172 for the compounds of Formula (I); and in U.S. Pat. Nos. 4,806,549, 4,806,550 and 5,952,504 and in EP 0 259 174 A1 and in WO 89/08104 and WO 92/12969 for the compounds of Formula (II); and in U.S. Pat. Nos. 5,686,458, 5,750,531 and 5,990,311 and in WO 98/18784 and WO 98/43968 for the compounds of Formula (III); and in U.S. Pat. No. 5,677,302 for the compounds of Formula (IV); and in WO 97/32854 for the compounds of Formula (V); and in U.S. Pat. Nos. 4,818,760, 4,845,118, 4,871,734, 4,956,366 and 5,114,955 and in EP 0 234 485 A1 for the compounds of Formula (VI); and in U.S. Pat. Nos. 5,439,917 and 5,665,730 and in EP 0 033 094 B1 and in WO 95/27714 for the compounds of Formula (VII); the disclosures of each of which are incorporated by reference herein in their entirety.

The nitrosated and nitrosylated proton pump inhibitors of the present invention can be synthesized as shown in reaction Schemes 1 through 7 presented herein. The parent proton pump inhibitor compounds can be nitrosated and/or nitrosylated through one or more sites such as oxygen, sulfur, carbon and/or nitrogen using the methods described in the examples herein and using conventional methods known to one skilled in the art. For example, known methods for nitrosating and nitrosylating compounds are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety. The methods of nitrosating and/or nitrosylating the compounds described in the examples herein and in these references can be applied by one skilled in the art to produce any of the nitrosated and/or nitrosylated proton pump inhibitors described herein.

Nitroso or nitro compounds of formula (I), where X is a —ONO, —SNO, or —ONO$_2$ group and R, R$_2$, R$_3$, R$_4$, R$_5$, R$_{10}$, R$_{11}$, A, B, J, R$_e$, R$_f$, and p are as defined herein, and a nitrite, nitrate, or thionitrite containing carbamate is representative of the D$_1$ group, as defined herein, may be prepared as shown in Scheme 1. The substituted imidazole nitrogen group of formula 1 is converted to the anion by treatment with one equivalent of a strong non-nucleophilic base, such as sodium hydride or potassium hydride, in an aprotic solvent, such as tetrahydrofuran (THF) or dimethylformamide (DMF). The carbamate of formula IA, IB, or IC where p, X, Re and R$_1$ are as defined herein, is prepared by reacting the imidazole anion with a suitably functionalized chloroformate in an inert solvent, such as THF or DMF.

Typically the coupling reaction is performed at a temperature ranging from −78° C. to room temperature. Preferred methods for the formation of chloroformates are reacting one equivalent of a X functionalized alcohol with one equivalent of phosgene at a temperature ranging from −78° C. to 0° C. in an inert solvent, such as ether or THF and in the presence of an amine base, such as pyridine or triethylamine. Removal of the amine hydrochloride by filtration affords a solution of the desired chloroformate which may be used directly or concentrated and redissolved in the anhydrous solution of choice prior to the coupling reaction with the imidazole anion to afford the carbamate of formula IA, IB, or IC.

On occasion it might be desirable to nitrosylate the alcohol or thiol after coupling a chloroformate to the imidazole anion. The chloroformate would be prepared by reacting phosgene with an alcohol containing a protected alcohol or thiol moiety. Preferred protecting groups for an alcohol moiety are silyl ethers, such as a trimethylsilyl ether, a tert-butyldimethylsilyl ether, or a tert-butyldiphenylsilyl ether. After formation of the carbamate, deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine affords the compound of formula IA. Preferred protecting groups for the thiol moiety are as a thioester, such as a thioacetate or a thiobenzoate or as a disulfide. Deprotection of the thiol moiety (zinc in dilute aqueous acid, triphenylphosphine in water and sodium borohydride are preferred methods for reducing disulfide groups while aqueous base or sodium methoxide in methanol is typically used to hydrolyze thioesters) followed by reaction with a suitable nitrosylating agent such, as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of formula IB. Nitrosation of the carbamate product may be accomplished by first converting the deprotected alcohol to a leaving group such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccinimide, in an inert solvent, such as THF. Treatment of the bromide or iodide with silver nitrate in an inert solvent, such as acetonitrile, affords the compound of formula IC. Alternatively, the halide containing carbamate may be formed directly by preparing a halide containing chloroformate from a halide containing alcohol. Preferred halides are bromide and iodide. Coupling of the imidazole anion with the halide containing chloroformate followed by reaction of the carbamate product with silver nitrate in an inert solvent, such as acetonitrile, affords the compound of formula IC.

Scheme 1

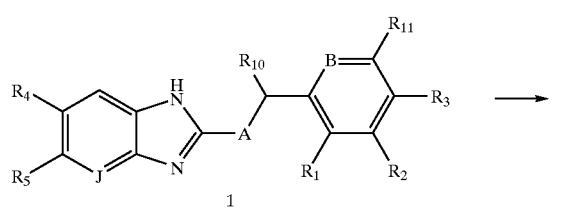

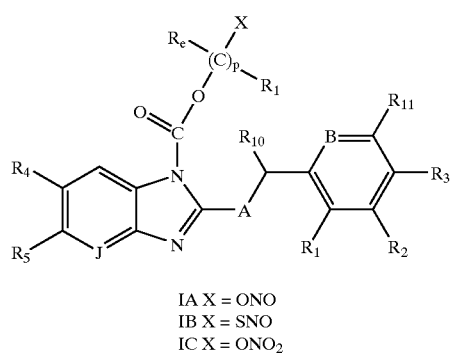

IA X = ONO
IB X = SNO
IC X = ONO$_2$

Nitroso or nitro compounds of formula (II), where X is a —ONO, —SNO, or —ONO$_2$ group and $R_8$, $R_9$, $R_{71}$, $D_1$, J, $R_e$, $R_f$, o, p, and q are as defined herein, and a nitrite, nitrate, or thionitrite containing alkoxyethyl ester is representative of the K group, as defined herein, may be prepared as shown in Scheme 2. The hydroxyl group of formula 2 is converted to the ester of formula IIA, IIB, or IIC, where p, $R_e$, $R_f$ and X are as defined herein, by reaction with an appropriate nitrite, thionitrite, or nitrate containing activated acylating agent. Preferred methods for the formation of esters are reacting the alcohol with the preformed acid chloride or anhydride of the nitrite, thionitrite, or nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate such as isobutylchloroformate in the presence of an amine base, such as triethylamine in an inert solvent, such as ether, THF, dichloromethane, or toluene. Alternatively, the alcohol and nitrite, thionitrite, or nitrate containing acid may be condensed in the presence of a dehydrating agent, such as dicyclohexylcarbodiimide (DCC) or 1-ethyl-3 (3-dimethylaminopropyl) carbodiimide hydrochloride (EDAC.HCl) with or without a catalyst, such as 4-dimethylaminopyridine (DMAP) or 1-hydroxybenzotriazole (HOBt).

On occasion it might be desirable to nitrosylate the alcohol or thiol after coupling the activated acylating agent to the alcohol. The activated acylating agent would be prepared from an acid containing a protected alcohol or thiol moiety. Preferred protecting groups for an alcohol moiety are silyl ethers, such as a trimethylsilyl ether, a tert-butyldimethylsilyl ether, or a tert-butyldiphenylsilyl ether. After formation of the ester, deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of formula IIA. Preferred protecting groups for the thiol moiety are as a thioester, such as a thioacetate or a thiobenzoate, or as a disulfide. Deprotection of the thiol moiety (zinc in dilute aqueous acid, triphenylphosphine in water and sodium borohydride are preferred methods for reducing disulfide groups while aqueous base or sodium methoxide in methanol is typically used to hydrolyze thioesters) followed by reaction with a suitable nitrosylating agent such, as thionyl chloride nitrite or thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of formula IIB. Nitrosation of the ester product may be accomplished by first converting the deprotected alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccinimide, in an inert solvent, such as THF. Treatment of the bromide or iodide with silver nitrate in an inert solvent, such as acetonitrile affords the compound of formula IIC. Alternatively, the halide containing ester may be formed directly by preparing a halide containing active acylating agent from a halide containing acid. Preferred halides are bromide and iodide.

Coupling of the alcohol with the halide containing active acylating agent followed by reaction of the ester product with silver nitrate in an inert solvent, such as acetonitrile affords the compound of formula IIC. Preferred coupling methods for the formation of esters from alcohols are those methods described herein (e.g. with the preformed acid-chloride or anhydride or with the carboxylic acid and a dehydration agent, such as DCC or EDAC.HCl).

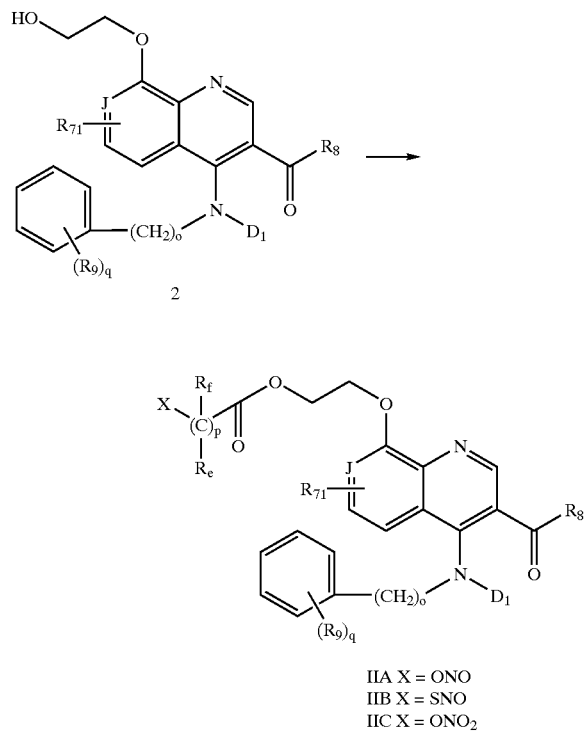

IIA X = ONO
IIB X = SNO
IIC X = ONO$_2$

Nitroso or nitro compounds of formula (III), where X is a —ONO, —SNO, or —ONO$_2$ group and $R_{14}$, $R_{17}$, $A_1$, $A_2$, $A_3$, $R_e$, $R_f$, $Y_3$, and p, are as defined herein, and a nitrite, nitrate, or thionitrite containing acyloxymethyl ester is representative of the $R_{13}$ group may be prepared as shown in Scheme 3. The hydroxyl group of formula 3 is converted to the ester of formula IIIA, IIIB, or IIIC, where p, $R_e$, $R_f$ and X are as defined herein, by reaction with an appropriate nitrite, thionitrite, or nitrate containing activated acylating agent. Preferred methods for the formation of esters are reacting the alcohol with the preformed acid chloride or symmetrical anhydride of the nitrite, thionitrite, or nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate, such as isubutylchloroformate, in the presence of an amine base, such as triethylamine in an inert solvent, such as ether, THF, dichloromethane, or toluene. Alternatively, the alcohol and nitrite, thionitrite, or nitrate containing acid may be condensed in the presence of a dehydrating agent, such as DCC or EDAC.HCl with or without a catalyst, such as DMAP or HOBt.

On occasion it might be desirable to nitrosylate the alcohol or thiol after coupling the activated acylating agent to the alcohol. The activated acylating agent would be prepared from an acid containing a protected alcohol or thiol moiety. Preferred protecting groups for an alcohol moiety are silyl ethers, such as a trimethylsilyl ether, a tert-butyldimethylsilyl ether, or a tert-butyldiphenylsilyl ether. After formation of the ester, deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine affords the compound of formula IIIA. Preferred protecting groups for the thiol moiety are as a thioester, such as a thioacetate or a thiobenzoate or as a disulfide. Deprotection of the thiol moiety (zinc in dilute aqueous acid, triphenylphosphine in water and sodium borohydride are preferred methods for reducing disulfide groups while aqueous base or sodium methoxide in methanol is typically used to hydrolyze thioesters) followed by reaction with a suitable nitrosylating agent such, as thionyl chloride nitrite or thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of formula IIIB. Nitrosation of the ester product may be accomplished by first converting the deprotected alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccinimide, in an inert solvent, such as THF. Treatment of the bromide or iodide with silver nitrate in an inert solvent, such as acetonitrile, affords the compound of formula IIIC. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate in an inert solvent, such as acetonitrile, affords the compound of formula IIIC. Preferred coupling methods for the formation of esters from alcohols are those methods described herein (e.g. with the preformed acid chloride or anhydride or with the carboxylic acid and a dehydration agent, such as DCC or EDAC.HCl).

Scheme 3

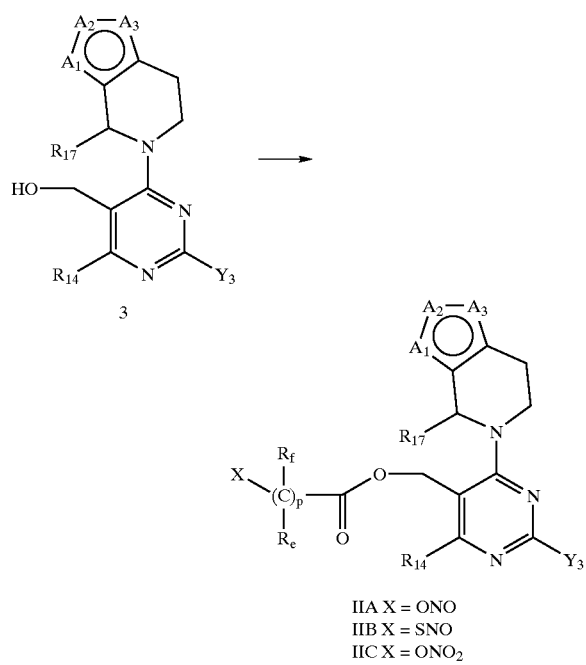

IIA X = ONO
IIB X = SNO
IIC X = ONO₂

Nitroso or nitro compounds of formula (IV), where X is a —ONO, —SNO, or —ONO₂ group and $R_{18}$, $R_{19}$, $R_e$, $R_f$, and p, are as defined herein, and a nitrite, nitrate, or thionitrite containing carboxylic acid ester is representative of the $X_4$ group may be prepared as shown in Scheme 4. The acid of the formula 4 is converted to the ester of formula IVA, IVB, or IVC, where p, $R_e$, $R_f$ and X are as defined herein, by reaction with an appropriate nitrite, thionitrite, or nitrate containing alcohol. Preferred methods for the preparation of esters are initially forming the mixed anhydride via reaction of 4 with a chloroformate, such as isobutylchloroformate, in the presence of a non nucleophilic base, such as triethylamine, in an anhydrous inert solvent, such as dichloromethane, diethylether or THF. The mixed anhydride is then reacted with the nitrite, thionitrite, or nitrate containing alcohol preferably in the presence of a condensation catalyst, such as DMAP. Alternatively, the acid 4 may be first converted to the acid chloride by treatment with oxalyl chloride in the presence of a catalytic amount of DMF. The acid chloride is then reacted with the nitrite, thionitrite, or nitrate containing alcohol preferably in the presence of a condensation catalyst, such as DMAP, and a tertiary amine base, such as triethylamine, to afford the ester of formula IVA, IVB, or IVC. Alternatively, the acid 4 and nitrite, thionitrite, or nitrate containing alcohol may be coupled to afford the ester of formula IVA, IVB, or IVC by treatment with a dehydration agent, such as DCC or EDAC.HCl, with or without a catalyst, such as DMAP or HOBt.

On occasion it might be desirable to nitrosylate the alcohol or thiol after coupling the acid to the alcohol. The ester would be prepared by reacting the carboxylic acid with an alcohol containing a protected alcohol or thiol moiety. Preferred protecting groups for an alcohol moiety are silyl ethers, such as a trimethylsilyl ether, a tert-butyldimethylsilyl ether, or a tert-butyldiphenylsilyl ether. After coupling the acid and alcohol moieties, deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of formula IVA. Preferred protecting groups for the thiol moiety are as a thioester, such as a thioacetate or a thiobenzoate or as a disulfide. Deprotection of the thiol moiety (zinc in dilute aqueous acid, triphenylphosphine in water and sodium borohydride are preferred methods for reducing disulfide groups while aqueous base or sodium methoxide in methanol is typically used to hydrolyze thioesters) followed by reaction with a suitable nitrosylating agent such, as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of formula IVB. Nitrosation of the ester product containing a deprotected alcohol moiety may be accomplished by first converting the alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluenesulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccimide, in an inert solvent, such as THF. Treatment of the bromide or iodide with silver nitrate in an inert solvent, such as acetonitrile, affords the compound of formula IVC. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate affords the compound of formula IVC. Preferred coupling methods for the formation of esters from alcohols are those methods described herein (e.g. with the preformed acid chloride or anhydride or with the carboxylic acid and a dehydration agent, such as DCC or EDAC.HCl).

Scheme 4

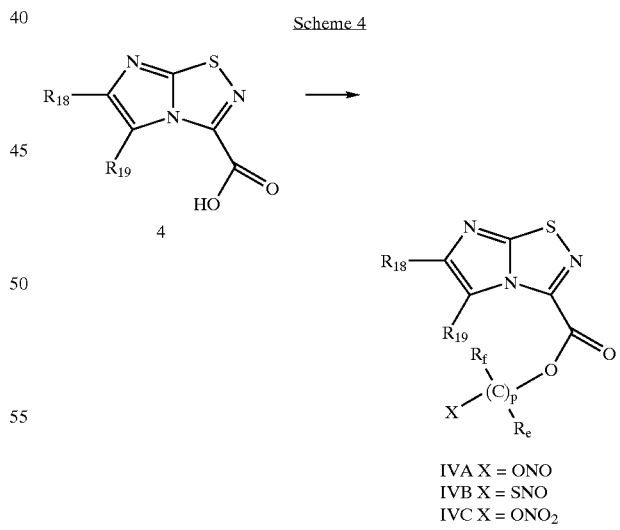

IVA X = ONO
IVB X = SNO
IVC X = ONO₂

Nitroso or nitro compounds of formula (V), where X is a —ONO, —SNO, or —ONO₂ group and $R_{23}$, $R_{24}$, $R_{25}$, $R_{27}$, $R_{29}$, $R_{30}$, $R_e$, $R_f$, n and p, are as defined herein, and a nitrite, nitrate, or thionitrite containing ester of a substituted pyridine is representative of the $X_5$ group may be prepared as shown in Scheme 5. The hydroxyl group of formula 5 is converted to the ester of formula VA, VB, or VC, where p, $R_e$, $R_f$ and X are as defined herein, by reaction with an appropriate nitrite, thionitrite, or nitrate containing activated acylating agent. Preferred methods for the formation of esters are reacting the alcohol with the preformed acid chloride or symmetrical anhydride of the nitrite, thionitrite, or nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate, such as isobutylchloroformate, in the presence of an amine base, such as triethylamine, in an inert solvent, such as ether, THF, dichloromethane, or toluene. Alternatively, the alcohol and nitrite, thionitrite, or nitrate containing acid may be condensed in the presence of a dehydrating agent, such as DCC or EDAC.HCl, with or without a catalyst, such as DMAP or HOBt.

On occasion it might be desirable to nitrosylate the alcohol or thiol after coupling the activated acylating agent to the alcohol. The activated acylating agent would be prepared from an acid containing a protected alcohol or thiol moiety. Preferred protecting groups for an alcohol moiety are silyl ethers, such as a trimethylsilyl ether, a tert-butyldimethylsilyl ether, or a tert-butyldiphenylsilyl ether. After formation of the ester, deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine affords the compound of formula VA. Preferred protecting groups for the thiol moiety are as a thioester, such as a thioacetate or a thiobenzoate or as a disulfide. Deprotection of the thiol moiety (zinc in dilute aqueous acid, triphenylphosphine in water and sodium borohydride are preferred methods for reducing disulfide groups while aqueous base or sodium methoxide in methanol is typically used to hydrolyze thioesters) followed by reaction with a suitable nitrosylating agent, such as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of formula VB. Nitrosation of the ester product may be accomplished by first converting the deprotected alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine in the presence of a halide source, such as carbon tetrabromide or N-iodosuccimide in an inert solvent, such as THF. Treatment of the bromide or iodide with silver nitrate in an inert solvent, such as acetonitrile, affords the compound of formula VC. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate in an inert solvent, such as acetonitrile, affords the compound of formula VC. Preferred coupling methods for the formation of esters from alcohols are those methods described herein (e.g. with the preformed acid chloride or anhydride or with the carboxylic acid and a dehydration agent, such as DCC or EDAC.HCl).

Scheme 5

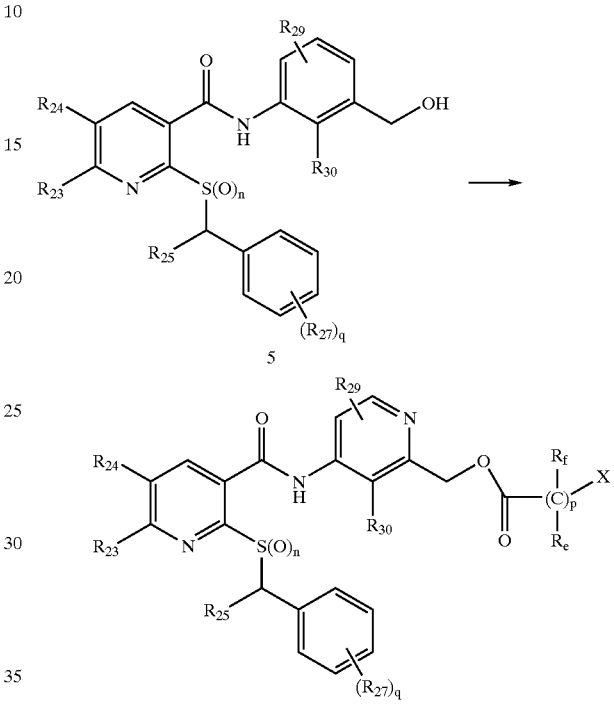

VA X = ONO
VB X = SNO
VC X = ONO$_2$

Nitroso or nitro compounds of formula (VI), where X is a —ONO, —SNO, or —ONO$_2$ group and $R_{26}$, $R_{35}$, $R_{36}$, A, $A_4$, $A_5$, $A_6$, $R_e$, $R_f$, and p are as defined herein, and a nitrite, nitrate, or thionitrite containing carbamate is representative of the $D_1$ group, as defined herein, may be prepared as shown in Scheme 6. The substituted imidazole nitrogen group of formula 6 is converted to the anion by treatment with one equivalent of a strong non-nucleophilic base, such as sodium hydride or potassium hydride in an aprotic solvent, such as THF or DMF. The carbamate of formula VIA, VIB, or VIC where p, X, $R_e$ and $R_f$ are as defined herein, is prepared by reacting the imidazole anion with a suitably functionalized chloroformate in an inert solvent, such as THF or DMF. Typically the coupling reaction is performed at a temperature ranging between −78° C. and room temperature. Preferred methods for the formation of cloroformates are reacting one equivalent of X functionalized alcohol with one equivalent of phosgene at a temperature ranging from −78° C. to 0° C. in an inert solvent, such as ether or THF, and in the presence of an amine base, such as pyridine or triethylamine. Removal of the amine hydrochloride by filtration affords a solution of the desired chloroformate which may be used directly or concentrated and redissolved in the anhydrous solution of choice prior to the coupling reaction with the imidazole anion to afford the carbamate of the formula VIA, VIB, or VIC.

On occasion it might be desirable to nitrosylate the alcohol or thiol after coupling a chloroformate to the imidazole anion. The chloroformate would be prepared by reacting phosgene with an alcohol containing a protected alcohol or thiol moiety. Preferred protecting groups for an alcohol moiety are silyl ethers, such as a trimethylsilyl ether, a tert-butyldimethylsilyl ether, or a tert-butyldiphenylsilyl ether. After formation of the carbamate, deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine, affords the compound of formula VIA. Preferred protecting groups for the thiol moiety are as a thioester, such as a thioacetate or a thiobenzoate or as a disulfide. Deprotection of the thiol moiety (zinc in dilute aqueous acid, triphenylphosphine in water and sodium borohydride are preferred methods for reducing disulfide groups while aqueous base or sodium methoxide in methanol is typically used to hydrolyze thioesters) followed by reaction with a suitable nitrosylating agent, such as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of formula VIB. Nitrosation of the carbamate product may be accomplished by first converting the deprotected alcohol to a leaving group, such as a mesylate or a tosylate. This reaction is typically performed at a temperature of 0° C. to room temperature in an inert solvent, such as ether, THF, or dichloromethane, with the alcohol, methansulfonyl chloride or para-toluensulfonyl chloride, and an amine base, such as triethylamine or pyridine, as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine, in the presence of a halide source, such as carbon tetrabromide or N-iodosuccimide, in an inert solvent, such as THF. Treatment of the bromide or iodide with silver nitrate in an inert solvent such as acetonitrile affords the compound of formula VIC. Alternatively, the halide containing carbamate may be formed directly by preparing a halide containing chloroformate from a halide containing alcohol. Preferred halides are bromide and iodide. Coupling of the imidazole anion with the halide containing chloroformate followed by reaction of the carbamate product with silver nitrate in an inert solvent such as acetonitrile affords the compound of formula VIC.

Scheme 6

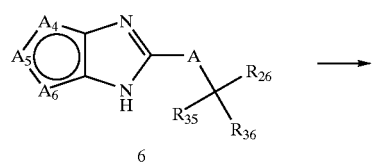

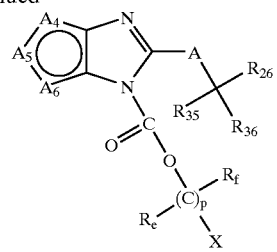

VIA X = ONO
VIB X = SNO
VIC X = $ONO_2$

Nitroso or nitro compounds of formula (VII), where X is a —ONO, —SNO, or —$ONO_2$ group and $R_{60}$, $A_7$, $X_7$, $Y_7$, $R_e$, $R_f$, and p, are as defined herein, and a nitrite, nitrate, or thionitrite containing acyl group is representative of the D group may be prepared as shown in Scheme 7. The hydroxyl group of formula 7 is converted to the ester of formula VIIA, VIIB, or VIIC, where p, $R_e$, $R_f$ and X are as defined herein, by reaction with an appropriate nitrite, thionitrite, or nitrate containing activated acylating agent. Preferred methods for the formation of esters are reacting the alcohol with the preformed acid chloride or symmetrical anhydride of the nitrite, thionitrite, or nitrate containing acid. Preferred methods for preparing acid chlorides are treating the carboxylic acid with oxalyl chloride and a catalytic amount of DMF in an inert solvent, such as ether, THF, dichloromethane, or toluene. Preferred methods for preparing mixed anhydride are reacting the carboxylic acid with a chloroformate, such as isobutylchloroformate, in the presence of an amine base, such as triethylamine, in an inert solvent, such as ether, THF, dichloromethane, or toluene. Alternatively, the alcohol and nitrite, thionitrite, or nitrate containing acid may be condensed in the presence of a dehydrating agent, such as DCC or EDAC.HCl with or without a catalyst, such as DMAP or HOBt.

On occasion it might be desirable to nitrosylate the alcohol or thiol after coupling the activated acylating agent to the alcohol. The activated acylating agent would be prepared from an acid containing a protected alcohol or thiol moiety. Preferred protecting groups for an alcohol moiety are silyl ethers, such as a trimethylsilyl ether, a tert-butyldimethylsilyl ether, or a tert-butyldiphenylsilyl ether. After formation of the ester, deprotection of the hydroxyl moiety (fluoride ion is the preferred method for removing silyl ether protecting groups) followed by reaction with a suitable nitrosylating agent, such as thionyl chloride nitrite, thionyl dinitrite, or nitrosonium tetrafluoroborate, in a suitable anhydrous solvent, such as dichloromethane, THF, DMF, or acetonitrile, with or without an amine base, such as pyridine or triethylamine affords the compound of formula VIIA. Preferred protecting groups for the thiol moiety are as a thioester, such as a thioacetate or a thiobenzoate or as a disulfide. Deprotection of the thiol moiety (zinc in dilute aqueous acid, triphenylphosphine in water and sodium borohydride are preferred methods for reducing disulfide groups while aqueous base or sodium methoxide in methanol is typically used to hydrolyze thioesters) followed by reaction with a suitable nitrosylating agent, such as thionyl chloride nitrite, thionyl dinitrite, a lower alkyl nitrite, such as tert-butyl nitrite, or nitrosonium tetrafluoroborate, in a suitable anhydrous solvent, such as methylene chloride, THF, DMF, or acetonitrile, with or without an amine base, such as pyridine or triethylamine, affords the compound of formula VIIB. Nitrosation of the ester product may be accomplished by first converting the deprotected alcohol to a leaving group, such as a mesylate or a tosylate. This reaction is typically performed at a temperature of 0° C. to room temperature in an inert solvent, such as ether, THF, or dichloromethane with the alcohol, methansulfonyl chloride or para-toluensulfonyl chloride, and an amine base, such as triethylamine or pyridine as the reactants. The corresponding iodide is then prepared by reacting the mesylate or tosylate with sodium iodide in acetone. The halide may also be formed from the alcohol by treatment of the hydroxyl moiety with a phosphorus reagent, such as triphenylphosphine in the presence of a halide source, such as carbon tetrabromide or N-iodosuccimide in an inert solvent, such as THF. Treatment of the bromide or iodide with silver nitrate in an inert solvent, such as acetonitrile, affords the compound of formula VIIC. Alternatively, the halide containing ester may be formed directly by preparing a halide containing active acylating agent from a halide containing acid. Preferred halides are bromide and iodide. Coupling of the alcohol with the halide containing active acylating agent followed by reaction of the ester product with silver nitrate in an inert solvent, such as acetonitrile, affords the compound of formula VIIC. Preferred coupling methods for the formation of esters from alcohols are those methods described herein (e.g. with the preformed acid chloride or anhydride or with the carboxylic acid and a dehydration agent, such as DCC or EDAC.HCl).

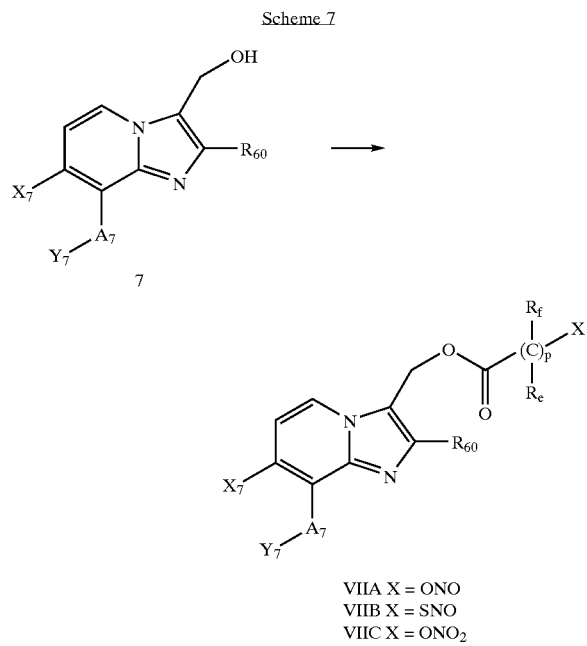

Scheme 7

VIIA X = ONO
VIIB X = SNO
VIIC X = ONO$_2$

The compounds of the present invention include proton pump inhibitors, such as those described herein, which have been nitrosated and/or nitrosylated through one or more sites such as oxygen (hydroxyl condensation), sulfur (sulfhydryl condensation), carbon and/or nitrogen. The nitrosated and/or nitrosylated proton pump inhibitors of the present invention are capable of donating, transferring and/or releasing a biologically active form of nitrogen monoxide (i.e., nitric oxide).

Nitrogen monoxide can exist in three forms: NO— (nitroxyl), NO. (uncharged nitric oxide) and NO⁺ (nitrosonium). NO. is a highly reactive short-lived species that is potentially toxic to cells. This is critical because the pharmacological efficacy of NO depends upon the form in which it is delivered. In contrast to the nitric oxide radical (NO.), nitrosonium (NO⁺) does not react with $O_2$ or $O_2^-$ species, and functionalities capable of transferring and/or releasing NO⁺ and NO— are also resistant to decomposition in the presence of many redox metals. Consequently, administration of charged NO equivalents (positive and/or negative) is a more effective means of delivering a biologically active NO to the desired site of action.

Compounds contemplated for use in the present invention (e.g., proton pump inhibitors optionally substituted with one or more NO and/or NO$_2$ groups) can be used in combination with nitric oxide and compounds that release nitric oxide (i.e., compounds that release nitric oxide or otherwise directly or indirectly deliver or transfer nitric oxide to a site of its activity, such as on a cell membrane, in vivo, and/or elevate or stimulate production of endogenous nitric oxide or EDRF in vivo and/or is a substrate for nitric oxide synthase). "In combination," as used herein can mean that (i) the proton pump inhibitor, optionally substituted with at least one. NO and/or NO$_2$ group, and nitric oxide donor can be present together in the same composition; (ii) the proton pump inhibitor, optionally substituted with at least one NO and/or NO$_2$ group, and nitric oxide donor can be administered separately; and/or (iii) the proton pump inhibitor, optionally substituted with at least one NO and/or NO$_2$ group, and nitric oxide donor can be together in the form of a kit.

The term "nitric oxide" encompasses uncharged nitric oxide (NO.) and charged nitrogen monoxide species, preferably charged nitrogen monoxide species, such as nitrosonium ion (NO⁺) and nitroxyl ion (NO—). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines (NONOates), (E)-alkyl-2-[(E)-hydroxyimino]-5-nitro-3-hexene amines or amides, nitrosoamines, furoxans as well as substrates for the endogenous enzymes which synthesize nitric oxide. The "NO adducts" can be mono-nitrosylated, poly-nitrosylated, mono-nitrosated and/or poly-nitrosated or a combination thereof at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Another embodiment of the present invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine and S-nitroso-glutathione.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;

(ii) $ONS(C(R_e)(R_f))_m R_e$; and (iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or $(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or —N(R$_a$)R$_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T—Q)(R$_e$)(R$_f$), or —(N$_2$O$_2$—).M$^+$, wherein M$^+$ is an organic or inorganic cation; with the proviso that when $R_i$ is CH$_2$—C(T—Q)(R$_e$)(R$_f$) or —(N$_2$O$_2$—).M$^+$; then "—T—Q" can be a hydrogen, an alkyl group, an alkoxyalkyl group, an aminoalkyl group, a hydroxy group or an aryl group.

In cases where $R_e$ and $R_f$ are a heterocyclic ring or taken together $R_e$ and $R_f$ are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with NaNO$_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the present invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C-heterocyclic compounds.

Another group of NO adducts for use in the present invention include nitrates that donate, transfer or release nitric oxide, such as compounds comprising at least one $O_2N$—O—, $O_2N$—N—, $O_2N$—S or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—N—, $O_2N$—S or $O_2N$—C— modified and unmodified oligonucleotides (comprising at least 5 nucleotides, preferably 5–200 nucleotides); $O_2N$—O—, $O_2N$—N—, $O_2N$—S or $O_2NC$— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityltetranitrate, mannitol hexanitrate, nitroglycerin, pentaerythritoltetranitrate, pentrinitrol and propatylnitrate.

Another group of NO adducts are N-oxo-N-nitrosoamines that donate, transfer or release nitric oxide and are represented by the formula: $R^1R^2$—N(O—M$^+$)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where M$^+$ is an organic or inorganic cation, such as, for example, an alkyl substituted ammonium cation or a Group I metal cation.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO—) and uncharged nitric oxide (NO.). Compounds where the thiol groups are not sufficiently close to form disulfide bridges generally provide nitric oxide as the NO— form and not as the uncharged NO. form.

The present invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature,* 327:524–526 (1987); Ignarro et al, *Proc. Natl. Acad. Sci. USA,* 84:9265–9269 (1987)).

Another aspect of the invention provides methods for preventing and/or treating gastrointestinal disorders by administering to the patient in need thereof a therapeutically effective amount of the compounds and/or compositions described herein. Such gastrointestinal disorders include, for example, inflammatory bowel disease, Crohn's disease, irritable bowel syndrome, ulcerative colitis, peptic ulcers, stress ulcers, bleeding peptic ulcers, duodenal ulcers, infectious enteritis, colitis, diverticulitis, gastric hyperacidity, dyspepsia, gastroparesis, Zollinger-Ellison syndrome, gastroesophageal reflux disease, *Helicobacter Pylori* associated disease, short-bowel (anastomosis) syndrome, hypersecretory states associated with systemic mastocytosis or basophilic leukemia and hyperhistaminemia that result, for example, from neurosurgery, head injury, severe body trauma or burns. In one aspect of the invention; the patient can be administered at least one nitrosated and/or nitrosylated proton pump inhibitor of the invention to prevent and/or treat the gastrointestinal disorder. In another aspect of the invention, the patient can be administered at least one antacid and at least one nitrosated and/or nitrosylated proton pump inhibitor of the invention to prevent or treat the gastrointestinal disorder. In another aspect of the invention, the patient can be administered at least one nitrosated and/or nitrosylated proton pump inhibitor of the invention and at least one compound that donates, transfers or releases nitric oxide, or elevates endogenous levels of nitric oxide or EDRF, or is a substrate for nitric oxide synthase, to prevent and/or treat the gastrointestinal disorder. In still another aspect of the invention, the patient can be administered at least one antacid, at least one nitrosated and/or nitrosylated proton pump inhibitor of the invention, and at least one compound that donates, transfers or releases nitric oxide, or elevates endogenous levels of nitric oxide or EDRF, or is a substrate for nitric oxide synthase, to prevent and/or treat the gastrointestinal disorder. In yet another aspect of the present invention, the patient can be administered at least one proton pump inhibitor and at least one compound that donates, transfers or releases nitric oxide, or elevates endogenous levels of nitric oxide or EDRF, or is a substrate for nitric oxide synthase, to prevent and/or treat the gastrointestinal disorder. In yet another aspect of the present invention, the patient can be administered at least one antacid, at least one proton pump inhibitor, and at least one compound that donates, transfers or releases nitric oxide, or elevates endogenous levels of nitric oxide or EDRF, or is a substrate for nitric oxide synthase, to prevent and/or treat the gastrointestinal disorder.

The antacid, proton pump inhibitor that is optionally substituted with at least one NO and/or $NO_2$ group, and/or the nitric oxide donor can be administered separately or as components of the same composition. These compounds and/or compositions can also be provided in the form of a pharmaceutical kit. The proton pump inhibitors substituted with at least one NO and/or $NO_2$ group and preferred nitric oxide donors are described in detail herein. Appropriate antacids for use in this aspect of the invention include any antacid known in the art, including, for example, aluminum hydroxide, magnesium hydroxide, magnesium carbonate, calcium carbonate and co-dried gels, such as, for example, aluminum hydroxide-magnesium carbonate co-dried gel.

Another aspect of the present invention provides methods to improve the gastroprotective properties, anti-*Helicobacter* properties and antacid properties of proton pump inhibitors by administering to a patient in need thereof a therapeutically effective amount of the compounds and/or compositions described herein. In one aspect of the invention, the patient can be administered at least one nitrosated and/or nitrosylated proton pump inhibitor of the invention to improve the gastroprotective properties, anti-*Helicobacter* properties and antacid properties of the proton pump inhibitor. In another aspect of the invention, the patient can be administered a bismuth-complex comprising at least one nitrosated and/or nitrosylated proton pump inhibitor of the invention to improve the gastroprotective properties, anti-*Helicobacter* properties and antacid properties of the proton pump inhibitor. In another aspect of the invention, the patient can be administered at least one nitrosated and/or nitrosylated proton pump inhibitor of the invention and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the proton pump inhibitor. In another aspect of the invention, the patient can be administered a bismuth complex comprising at least one nitrosated and/or nitrosylated proton pump inhibitor of the invention and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the proton pump inhibitor. In yet another aspect of the invention, the patient can be administered at least one proton pump inhibitor and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the proton pump inhibitor. In yet another aspect of the present invention, the patient can be administered a bismuth-complex comprising at least one proton pump inhibitor and at least one compound that donates, transfers or releases nitric oxide, or elevates endogenous levels of nitric oxide or EDRF, or is a substrate for nitric oxide synthase, to improve the gastroprotective properties, anti-*Helicobacter* properties and antacid properties of the proton pump inhibitor.

The bismuth-containing reagent, proton pump inhibitor, that is optionally, substituted with at least one NO and/or $NO_2$ group, and/or nitric oxide donor can be administered separately or as components of the same composition. The proton pump inhibitors, optionally substituted with at least one NO and/or $NO_2$ group, and nitric oxide donors are described in detail herein. Bismuth complexes are prepared by boiling the aqueous solution of the free base of the proton pump inhibitor with at least one bismuth-containing reagent, including, for example, bismuth citrate, bismuth salicylate, bismuth tartaric acid or mixtures thereof as described in U.S. Pat. No. 5,403,830 and in Ivanov et al, *J. Pharm. Pharmacol.*, 48:297–301 (1996), the disclosures of which are incorporated by reference herein in their entirety.

Another aspect of the present invention provides methods to facilitate ulcer healing and decrease the recurrence of ulcers by administering to a patient in need thereof a therapeutically effective amount of the compounds and/or compositions described herein. In one aspect of the invention, the patient can be administered at least one nitrosated and/or nitrosylated proton pump inhibitor of the invention to facilitate ulcer healing and decrease the recurrence of ulcers. In another aspect of the invention, the patient can be administered at least one nitrosated and/or nitrosylated proton pump inhibitor of the invention and at least one compound that donates, transfers or releases nitric oxide, or elevates endogenous levels of nitric oxide or EDRF, or is a substrate for nitric oxide synthase to facilitate ulcer healing and decrease the recurrence of ulcers. In yet another aspect of the invention, the patient can be administered at least one proton pump inhibitor and at least one compound that donates, transfers or releases nitric oxide, or elevates endogenous levels of nitric oxide or EDRF, or is a substrate for nitric oxide synthase, to facilitate ulcer healing and decrease the recurrence of ulcers. The proton pump inhibitor, that is optionally, substituted with at least one NO and/or $NO_2$ group, and/or nitric oxide donor can be administered separately or as components of the same composition. The proton pump inhibitor, optionally substituted with at least one NO and/or $NO_2$ group, and nitric oxide donors are described in detail herein.

Another aspect of the present invention provides methods to decrease or reverse gastrointestinal toxicity and facilitate ulcer healing resulting from, for example, the administration of nonsteroidal antiinflammatory drugs (NSAIDs), selective COX-2 inhibitors, and the like. In particular, the present invention provides methods of administering a therapeutically effective amount of the compounds and/or compositions described herein, and, optionally, administering a therapeutically effective amount of at least one NSAID or selective COX-2 inhibitor. In one aspect of the invention, the patient can be administered at least one nitrosated and/or nitrosylated proton pump inhibitor of the invention, and, optionally, at least one NSAID and/or selective COX-2 inhibitor, to decrease or reverse gastrointestinal toxicity and/or to facilitate ulcer healing resulting from the NSAID and/or selective COX-2 inhibitor treatment. In another aspect of the invention, the patient can be administered at least one NSAID and/or selective COX-2 inhibitor with a therapeutically effective amount of at least one nitrosated and/or nitrosylated proton pump inhibitor of the invention and at least one compound that donates, transfers or releases nitric oxide, or elevates endogenous levels of nitric oxide or EDRF, or is a substrate for nitric oxide synthase, to decrease or reverse gastrointestinal toxicity and/or to facilitate ulcer healing resulting from the NSAID and/or selective COX-2 inhibitor treatment. In yet another aspect of the present invention, the patient can be administered at least one NSAID and/or selective COX-2 inhibitor with a therapeutically effective amount of at least one proton pump inhibitor and at least one compound that donates, transfers or releases nitric oxide, or elevates endogenous levels of nitric oxide or EDRF, or is a substrate for nitric oxide synthase, to decrease or reverse gastrointestinal toxicity and/or to facilitate ulcer healing resulting from the NSAID and/or selective COX-2 inhibitor treatment. The NSAID and/or selective COX-2 inhibitor, nitrosated and/or nitrosylated proton pump inhibitor, proton pump inhibitor, and/or nitric oxide donor can be administered separately or as components of the same composition. These compounds and/or compositions can also be provided in the form of a pharmaceutical kit.

The compounds and compositions of the present invention can be used in this aspect of the invention with any NSAID and selective COX-2 inhibitor known in the art. Such NSAIDs include, for example, aspirin (e.g., acetylsalicylic acid), salicylate esters and salts, acetate esters of salicylic acid, difluorophenyl derivatives (e.g., diflunisal), salicylsalicylic acids (e.g., salsalate), salts of salicylic acids (e.g., sodium salicylate), salicylamide, sodium thiosalicylate, choline salicylate, magnesium salicylate, combinations of choline and magnesium salicylates, 5-aminosalicylic acid (e.g., mesalamine), salicylazosulfapyridine (e.g., sulfasalazine), methylsalicylate, and the like.

Another group of NSAIDs are the pyrazolon derivatives, which include, for example, phenylbutazone, oxyphenbutazone, antipyrine, aminopyrine, dipyrone and apazone (azapropazone). Another group of NSAIDs are the para-aminophenol derivatives, which are the so-called "coal tar" analgesics, including, for example, phenacetin and its active metabolite acetaminophen. Another group of compounds include indomethacin, a methylated indole derivative, and the structurally related compound sulindac. Yet another group of compounds is the fenamates which are derivatives of N-phenylanthranilic acid (e.g., mefenamic, meclofenamic, flufenamic, tolfenamic and etofenamic acids). Another contemplated NSAID is tolmetin.

Another group of NSAIDs are the propionic acid derivatives. Principal members of this group are, for example, ibuprofen, naproxen, flurbiprofen, fenoprofen and ketoprofen. Other members of this group include, for example, fenbufen, pirprofen, oxaprozin, indoprofen and tiaprofenic acid.

Still other NSAIDs are piroxicam, ampiroxicam, oxicam derivatives (which are a class of antiinflammatory enolic acids), tenoxicam tenidap, diclofenac (one of the series of phenylacetic acid derivatives that have been developed as antiinflammatory agents). Other NSAIDs include etodolac and nabumentone.

Selective COX-2 inhibitors are disclosed in, for example, U.S. Pat. Nos. 5,681,842, 5,750,558, 5,756,531, 5,776,984 and in WO 98/39330, WO 99/10331 and WO 99/10332 assigned to Abbott Laboratories; and in WO 98/50075 assigned to Algos Pharmaceutical Corporation; and in U.S. Pat. No. 5,980,905 assigned to AMBI Inc.; and in U.S. Pat. Nos. 5,776,967, 5,824,699, 5,830,911 and in WO 98/04527 and WO 98/21195 assigned to American Home Products Corporation; and in WO 99/18960 assigned to Astra Pharmaceuticals Ltd.; and in U.S. Pat. No. 5,905,089 assigned to Board of Supervisors of Louisiana State University; and in WO 97/13767 assigned to Chemisch Pharmazeutische Forschungsgesellschaft MBH; and in WO 96/10021 assigned to The Du Pont Merck Pharmaceutical Company; and in WO 99/13799 assigned to Euro-Celtique; and in U.S. Pat. No. 5,134,142 and in WO 99/15505 assigned to Fujisawa Pharmaceutical Co. Ltd.; and in U.S. Pat. Nos. 5,344,991, 5,393,790, 5,521,207, 5,596,008, 5,616,601, 5,620,999, 5,633,272, 5,643,933, 5,686,470, 5,696,143, 5,700,816, 5,859,257, 5,972,986, 5,990,148 and in WO 94/15932, WO 94/27980, WO 95/15316, WO 96/16934, WO 96/25405, WO 96/38418, WO 96/38442, WO 96/41645, WO 97/38986, WO 98/06708, WO 98/43649, WO 98/47509, WO 98/47890 and WO 99/22720 assigned to G. D. Searle & Co.; and in WO 96/31509 and WO 99/12930 assigned to Glaxo Group Limited; and in WO 97/34882 assigned to Grupo Farmaceutico Almirall; and in WO 97/03953 assigned to Hafslund Nycomed Pharma AG; and in U.S. Pat. Nos. 5,945,539, 5,994,381 and in EP 0 745 596 A1 assigned to Japan Tobacco, Inc.; and in U.S. Pat. Nos. 5,686,460, 5,807,873 and in WO 97/37984 and WO 99/21585 assigned to Laboratoires USPA; and in U.S. Pat. Nos. 5,585,504, 5,840,924, 5,883,267, 5,925,631 and in WO 97/44027, WO 97/44028, WO 97/45420, WO 98/00416, WO 98/47871, WO 99/15503, WO 99/15513, WO 99/20110, WO 99/45913 and WO 99/55830 assigned to Merck & Co. Inc.; and in U.S. Pat. Nos. 5,409,944, 5,436,265, 5,474,995, 5,536,752, 5,550,142, 5,510,368, 5,521,213, 5,552,422, 5,604,253, 5,604,260, 5,639,780, 5,677,318, 5,691,374, 5,698,584, 5,710,140, 5,733,909, 5,789,413, 5,817,700, 5,840,746, 5,849,943, 5,861,419, 5,994,379 and in EP 0 788 476 B1, EP 0 863 134 A1 and in WO 94/20480, WO 94/13635, WO 94/26731, WO 95/00501, WO 96/19469, WO 96/37467, WO 97/14691, WO 97/16435, WO 97/28120, WO 97/28121, WO 97/36863, WO 98/03484, WO 98/43966, WO 99/14194, WO 99/14195 and WO 99/23087 assigned to Merck Frosst Canada & Co., and in WO 99/59635 assigned to Merck Sharp & Dohme Limited; and in U.S. Pat. No. 5,380,738 assigned to Monsanto Company; and in WO 99/33796 assigned to Nissin Food Products Co. Ltd.; and in U.S. Pat. No. 5,783,597 assigned to Ortho Pharmaceutical Corporation; and in WO 98/07714 assigned to Oxis International Inc.; and in EP 0 937 722 A1 and in WO 98/50033 and WO 99/05104 assigned to Pfizer Inc.; and in U.S. Pat. No. 5,908,858 assigned to Sankyo Company Limited; and in WO 97/25045 assigned to Smithkline Beecham Corporation; and in U.S. Pat. No. 5,475,021 assigned to Vanderbilt University; and in WO 99/59634 assigned to Wakamoto Pharmaceutical Co. Ltd., the disclosures of each of which are incorporated by reference herein in their entirety.

Each of the above NSAIDs and selective COX-2 inhibitors is described more fully in the literature, such as in Goodman and Gilman, The Pharmacological Basis of Therapeutics (8th Edition), McGraw-Hill, pages 617–657 (1993); Merck Index on CD-ROM, Twelfth Edition, Version 12:1, (1996); STN Express, file phar and file registry, the disclosures of which are incorporated by reference herein in their entirety.

Other NSAIDs and selective COX-2 inhibitors that can be used in the present invention include those described in U.S. Pat. No. 5,703,073, and co-pending application Ser. No. 09/441,891 and 60/171,623, the disclosures of which are incorporated by reference herein in their entirety.

Another embodiment of the present invention provides methods to treat *Helicobacter pylori* by administering one or more acid-degradable antibacterial compounds in combination with at least one proton pump inhibitor that is substituted with at least one NO and/or $NO_2$ group, and, optionally, a therapeutically effective amount of at least one compound that donates, transfers or releases nitric oxide and/or stimulates endogenous production of NO or EDRF in vivo. Alternatively, this embodiment provides administering one or more acid-degradable antibacterial compounds in combination with at least one proton pump inhibitor, and, a therapeutically effective amount of at least one compound that donates, transfers or releases nitric oxide and/or stimulates endogenous production of NO or EDRF in vivo. U.S. Pat. Nos. 5,629,305 and 5,599,794, the disclosures of each of which are incorporated by reference herein in their entirety, disclose treating or preventing gastrointestinal disorders resulting from *Helicobacter pylori* by administering proton pump inhibitors in combination with antibacterial compounds. The proton pump inhibitors increase the intragastric pH in the stomach, thereby increasing the bioavailability of the acid-labile antibacterial compound. The antibacterial compound(s), proton pump inhibitor(s), optionally substituted with at least one NO and/or $NO_2$ group, and/or nitric oxide donor(s) can be administered separately, or as components of the same composition. The compounds and/ or compositions can also be provided in the form of a kit. The proton pump inhibitors that are optionally substituted with at least one NO group and nitric oxide donors are described herein. The antibacterial compounds contemplated for use in this embodiment of the invention include any acid-degradable antibacterial compound that is known in the art, including, for example antibiotics, such as, for example, amoxycillin, penicillin, benzylpenicillin, erythromycin base, clarithromycin, and the like.

Yet another embodiment of the present invention provides methods to treat viral infections by administering at least one proton pump inhibitor that is substituted with at least one NO and/or $NO_2$ group, and, optionally, a therapeutically effective amount of at least one compound that donates, transfers or releases nitric oxide and/or stimulates endogenous production of NO or EDRF in vivo. Alternatively, this embodiment provides administering at least one proton pump inhibitor, and, a therapeutically effective amount of at least one compound that donates, transfers or releases nitric oxide and/or stimulates endogenous production of NO or EDRF in vivo. U.S. Pat. No. 5,945,425, the disclosure of which is incorporated by reference herein in its entirety, discloses treating viral infections by administering proton pump inhibitors. The proton pump inhibitor(s), optionally substituted with at least one NO and/or $NO_2$ group, and/or nitric oxide donor(s) can be administered separately, or as components of the same composition. The compounds and/ or compositions can also be provided in the form of a kit. The proton pump inhibitors that are optionally substituted with at least one NO group and nitric oxide donors are described herein.

The compounds and compositions of the present invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Transdermal compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the present invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, nixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances which increase the viscosity of the suspension and include, for example, sodium carboxymethyl cellulose, sorbitol and/or dextran. Optionally, the suspension may also contain stabilizers.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the present invention, including, for example, encapsulation in liposomes, microbubbles, emulsions, microparticles, microcapsules and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

The compounds and compositions of the present invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitrous (nitrite salt), nitric (nitrate salt), carbonic, sulfuric, phosphoric acid, and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine), and procaine and the like. All of these salts may be prepared by conventional means from the corresponding compound by reacting, for example, the appropriate acid or base with the compound.

"Therapeutically effective amount" refers to the amount of the proton pump inhibitor, that is optionally substituted with at least one NO and/or $NO_2$ group, nitric oxide donor, antacid, bismuth-complex, NSAID, selective COX-2 inhibitor and/or acid-degradable antibacterial compound, that is effective to achieve its intended purpose. While individual patient needs may vary, determination of optimal ranges for effective amounts of each of the compounds and compositions is within the skill of the art. Generally, the dosage required to provide an effective amount of the composition, and which can be adjusted by one of ordinary skill in the art will vary, depending on the age, health, physical condition, sex, weight, extent of the dysfunction of the recipient, frequency of treatment and the nature and scope of the dysfunction or disease.

The amount of a given proton pump inhibitor, that is optionally substituted with at least one NO and/or $NO_2$ group, which will be effective in the treatment of a particular disorder or condition will depend on the nature of the disorder or condition, and can be determined by standard clinical techniques, including reference to Goodman and Gilman, supra; The Physician's Desk Reference, Medical Economics Company, Inc., Oradell, N.J., 1995; and Drug Facts and Comparisons, Inc., St. Louis, Mo., 1993. The precise dose to be used in the formulation will also depend on the route of administration, and the seriousness of the disease or disorder, and should be decided by the physician and the patient's circumstances.

The amount of nitric oxide donor in a pharmaceutical composition can be in amounts of about 0.1 to about 10 times the molar equivalent of the proton pump inhibitor. The usual daily doses of proton pump inhibitors are about 10 mg to about 400 mg per day and the doses of nitric oxide donors in the pharmaceutical composition can be in amounts of about 1 to about 500 mg/kg of body weight daily, preferably about 1 to about 50 mg/kg of body weight daily. Effective doses may be extrapolated from dose-response curves derived from in vitro or animal model test systems and are in the same ranges or less than as described for the commercially available compounds in the Physician's Desk Reference, supra.

The present invention also provides pharmaceutical kits comprising one or more containers filled with one or more of the ingredients of the pharmaceutical compounds and/or compositions of the present invention, including, at least, one or more of the proton pump inhibitors, that are optionally substituted with at least one NO moiety, and one or more of the NO donors described herein. Such kits can also include, for example, other compounds and/or compositions (e.g., NSAIDs, antacids and/or antibacterial compounds), a device(s) for administering the compounds and/or compositions, and written instructions in a form prescribed by a governmental agency regulating the manufacture, use or sale of pharmaceuticals or biological products, which instructions can also reflect approval by the agency of manufacture, use or sale for human administration.

EXAMPLES

Example 1

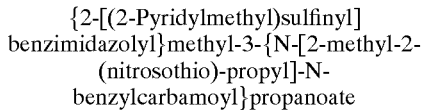

{2-[(2-Pyridylmethyl)sulfinyl]benzimidazolyl}methyl-3-{N-[2-methyl-2-(nitrosothio)-propyl]-N-benzylcarbamoyl}propanoate 1a. 2-Methyl-1-(benzylamino)propane-2-thiol A solution of α,α'-dithiodiisobutyraldehyde (10.31 g, 0.05 mol) and benzylamine (10.71 g, 0.10 mol) in chloroform (150 ml) was heated to reflux for 2 hours. The solution was cooled to room temperature, the chloroform was removed under vacuum and the residue was taken in up methanol (100 ml). Under ice cooling, sodium borohydride (6 g, 0.16 mol) was then added in portions over 1 hour and the resulting solution was stirred at room temperature for 1 hour. The reaction was concentrated under vacuum and the residue was partitioned between water (300 ml) and ethyl acetate (50 ml). The aqueous phase was extracted with ethyl ether (2×50 ml) and the combined organic phases were washed with brine and dried ($Na_2SO_4$). The volatiles were evaporated to give an oil (18.45 g, 95%) which was used directly in the next step. $^1$H NMR (300 MHz, $CDCl_3$): δ 1.29 (s, 12H), 2.57 (s, 4H), 3.81 (s, 4H), 7.21–7.33 (m, 10H). To a solution of the above oil (13.26 g, 0.034 mol) in ether (70 ml) and liquid ammonia (100 ml) cooled over a dry ice/acetone bath was added sodium until a blue color persisted for 40 min (~2 g of sodium was consumed). Ammonium chloride (15 g) was added and the reaction mixture was left overnight at room temperature. Water (100 ml) was added and the ether layer was separated. The aqueous phase was extracted with ether (2×50 ml) and the combined ether layers were washed with brine and dried ($Na_2SO_4$). The solvent was evaporated to give the title compound (12.83 g, 96.3%) as a colorless oil. $^1$H NMR (300 MHz, $CDCl_3$): δ 1.37 (s, 6H)! 2.61 (s, 2H), 3.86 (s, 2H), 7.22–7.36 (m, 5H); $^{13}$C NMR (75 MHz, $CDCl_3$) δ 30.58, 45.43, 54.24, 62.78, 126.86, 127.94, 128.34, 140.64; LCMS (m/e): 196 (M+1).

1b. 3-[N-(2-Methyl-2-sulfanylpropyl)-N-benzylcarbamoyl]propanoic acid

To a solution of the product of example 1a (4.52 g, 23.14 mmol) in dichloromethane (70 ml) at 0° C. was added succinic anhydride (2.20 g, 21.98 mmol). The reaction was stirred at room temperature overnight, washed with water (100 ml), the aqueous phase was extracted with dichloromethane (2×50 ml) and the combined organic phases were washed with brine and dried ($Na_2SO_4$). The solvent was evaporated under vacuum and the residue triturated with ether/hexane to give the title compound (6.46 g, 99.5%) as a white solid. mp. 123–126° C.; $^1$H NMR (300 MHz, $CDCl_3$): δ 1.40 and 1.47 (2 s, 6H), 1.82 (s, 1H), 2.65–2.86 (m, 4H), 3.47 and 3.61 (2 s, 2H), 4.89 and 4.93 (2 s, 2H), 7.137.54 (m, 5H), 10.41 (br s, 1H); $^{13}$C NMR (75 MHz, $CDCl_3$): δ 28.21, 29.39, 31.27, 46.43, 53.01, 58.51, 125.86, 127.50, 128.96, 136.52, 173.49, 177.63; LCMS (m/e): 296 (M+1).

1c. 3-{N-[2-Methyl-2-(nitrosothio)propyl)-N-benzylcarbamoyl]propanoic acid

To a solution of the product of example 1b (4.46 g, 15.1 mmol) in dichloromethane (100 ml) at 0° C. was added dropwise t-butyl nitrite (1.94 ml, 16.6 mmol). The resulting green solution was left at room temperature for 1 hour. The solvent was evaporated and hexane (20 ml) was added to the residue. The mixture was stored at −20° C. for 1 hour, then the hexane was decanted and the solid dried under vacuum to give pure the title compound (4.46 & 91.1%) as green crystals. mp. 95–98° C.; $^1$H NMR (300 MHz, CDCl$_3$): δ 1.91 and 1.98 (2 s, 6H), 2.63–2.78 (m, 4H), 4.07 and 4.19 (2 s, 2H), 4.60 and 4.80 (2 s, 2H), 7.06–7.37 (m, 5H); $^{13}$C NMR (75 MHz, CDCl$_3$): δ 27.65, 28.26, 29.33, 53.04, 55.74, 58.50, 125.96, 127.75, 129.07, 136.06, 173.81, 177.64; LCMS (m/e): 325 (M+1).

1d. {2-[(2-Pyridylmethyl)sulfinyl]benzimidazolyl}methyl-3-{N-[2-methyl-2(nitrosothio)-propyl]-N-benzylcarbamoyl}propanoate A mixture of timoprazole (0.51 g, 1.98 mmol) and 37% formaldehyde (0.80 ml) in acetonitrile (5 ml) was heated at 70° C. for 15 min. The reaction was evaporated to give a solid that was washed twice with ethyl ether/ethyl acetate (4:1) and dissolved in dichloromethane (10 ml). To this solution was added Example 1c (0.65 g, 2 mol), 4-(N—N-dimethylamino)pyridine (10 mg) and dicyclohexylcarbodiimide (1M in dichloromethane, 4 ml, 4 mmol). After stirring at room temperature for 3 hours, the reaction was concentrated under vacuum and the residue was purified by flash column chromatography (ethyl acetate/hexane, 4:1 to 7:1) to afford the title compound (0.65 g, 54.7%) as a green foam. $^1$H NMR (300 MHz, CDCl$_3$): δ1.82 and 1.91 (2 s, 6H), 2.63 and 2.75 (2br s, 4H), 4.08 and 4.13 (2 s, 2H), 4.70 and 4.85 (2 s, 2H), 4.88 (d, J=14 Hz, 1H), 4.92 (d, J=14 Hz, 1H), 6.36 (d, J=11.4 Hz, 1H), 6.42 (d, =11.4 Hz, 1H), 7.00 and 7.06 (2 d, J=6.8 Hz, 2H), 7.207.64 (m, 9H), 7.81 (d, !=7.7 Hz, 1H), 8.54 (d, J=4 Hz, 1H); $^{13}$C NMR (75 MHz, CDCl): δ 27.29, 27.94, 28.88, 52.58, 55.29, 58.18, 62.22, 65.04, 110.73, 120.73, 122.97, 123.85, 125.21, 125.30, 125.58, 127.41, 128.76, 135.03, 135.79, 136.66, 141.70, 149.71, 150.20, 151.66, 171.80, 172.76; LCMS (m/e): 594 (M+1).

EXAMPLE 2

{2-({[3-methyl-4-(2,2,2-trifluoroethyl)-2-pyridyl]methyl}sulfinyl) benzimidazolyl]-methyl-3-{N-[2-methyl-2-(nitrosothio)-propyl]-N-benzylcarbamoyl}propanoate 2a [2-({[3-methyl-4-(2,2,2-trifluoroethyl)-2-pyridyl]methyl}sulfinyl) benzimidazolyl]-methyl-3-{N-[2-methyl-2-(nitrosothio)-propyl]-N-benzylcarbamoyl}propanoate The procedure described in Example 1d was repeated using lansoprozole (0.739 g, 2 mmol) instead of timoprazole. The title compound (0.82 g, 59.4%) was obtained as a green foam. $^1$H NMR (300 MHz, CDCl$_3$): δ 1.84 and 1.92 (2 s, 6H), 2.28 (s, 3H), 2.65 and 2.76 (2 br s, 4H), 4.01 and 4.10 (2 s, 2H), 4.39 (q, J=7.3 Hz, 2H), 4.56 and 4.72 (2 s, 2H), 4.96 (d, J=14 Hz, 1H), 5.03 (d, =14 Hz, 1H), 6.46 (d, J=11 Hz, 1H), 6.54 (d, J=11 Hz, 1H), 6.65 (d, J=5 Hz, 1H), 7.00–7.40 (m, 7H), 7.64 (d, J=7.4 Hz, 1H), 7.80 (d, J=7.5 Hz, 1H), 8.25 (d, J=5 Hz, 1H); $^{13}$C NMR (75 MHz, CDCl): δ 24.85, 27.47, 28.13, 29.11, 33.82, 52.80, 55.53, 58.37, 59.81, 65.26 (q, J=36 Hz), 65.36, 105.81, 110.85, 120.93, 122.97, 123.92, 125.28, 125.78, 127.58, 128.93, 135.21, 136.01, 141.97, 148.09, 151.30, 152.81, 161.67, 171.96, 172.95; LCMS (m/e): 690 (M+1).

EXAMPLE 3

2-[2-(Nitrosothio)adamantan-2-yl]ethyl 2-({[3-methyl-4-(2,2,2-trifluoroethoxy)-2-pyridyl]methyl}sulfinyl)benzimidazolecarboxylate 3a. Adamantane-2-thione Adamantan-2-one (48.46 g, 322.6 mmol) in pyridine (300 mL) was heated to 90° C. and phosphorous pentasulfide (17.84 g, 40.13 mmol) was added. The reaction was maintained at 90° C. for two hours and at room temperature overnight during which time a precipitate formed. The pyridine solution was decanted and concentrated to dryness. The residual semisolid was treated with hexane (400 mL) to give an orange solution with a light brown suspension. The suspension was removed by filtration.

The filtrate was concentrated to dryness and dried to vacuum to give an orange solid (50.36 g). This crude product was purified by filtration through a pad of silica gel (hexane). $^1$H NMR (CDCl$_3$, 300 MHz): 83.43 (s, 2H), 2.1–1.9 (m, 12H); $^{13}$C NMR (75 MHz, CDCl$_3$): δ 222.4, 57.5, 41.1, 36.5, 27.4.

3b. tert-Butyl 2-(2-suifanyladamantan-2-yl)acetate

To t-butyl acetate (25 mL, 21.6 g, 186 mmol) in dry THF (400 mL) at −78° C. was added lithium diisopropylamide monotetrahydrofuran (1.5 M solution in cyclohexane, 100 mL, 150 mmol) under nitrogen and the reaction mixture was stirred at −78° C. for 40 minutes. The product of Example 3a (21.88 g, 131.57 mmol) in THF (400 mL) was added. The cold bath was removed and the reaction was stirred at room temperature for two hours. The reaction was diluted with methylene chloride and 2 M HCl (75 mL) was added. The organic phase was separated, washed with brine (4×40 mL), dried (MgSO$_4$), filtered, and concentrated. The crude product was purified by filtration through a pad of silica gel (5% EtOAc/95% hexane) to give the title compound (34.67 g, 122.7 mmol, 93%). R$_f$=0.48 (EtOAc/hexane 1:19); $^1$H NMR (CDCl$_3$, 300 MHz): δ 2.87 (s, 2H), 2.47 (d, l=11.5, 2H), 2.38 (s, 1H), 2.11 (d, J=11.9, 2H), 1.98 (s, 2H), 1.96 (m, 2H), 1.84–1.62 96 (m, 6H), 1.47 (s, 9H); $^{13}$C NMR (75 MHz, CDCl$_3$): δ 170.8, 80.7, 54.1, 47.3, 39.0, 38.2, 37.2, 36.6, 34.0, 33.3, 28.2, 27.5, 26.9. APIMS (1S, NH$_4$OAc) m/e 283 (MH$^+$); Anal. Calcd for C$_{16}$H$_{26}$O$_2$S (282.44): C, 68.04; H, 9.28 Found: C, 68.14; H, 9.30.

3c. 2-(2-Sulfanyladamantan-2-yl)ethan-1-ol

To a 0° C. cooled solution of Example 3b (4.1 g, 24.1 mmol) in anhydrous dichloromethane (40 mL) lithium aluminum hydride (1 M solution in THF) (40 mL) was added dropwise over a period of 20 minutes. The reaction mixture was stirred at 0° C. for further 15 minutes and then at room temperature for 30 minutes. The excess LiAlH$_4$ was destroyed by the addition of ethyl acetate. The reaction mixture was then poured over ice cold water, acidified with 1 N HCl and extracted with dichloromethane (2×200 mL). The combined extracts were washed with brine (1×75 mL), dried over sodium sulfate, filtered and solvent evaporated at reduced pressure to give the title compound (3.1 g), mp 68–70° C.; $^1$H NMR (CDCl$_3$): δ 1.16–1.9 (m, 11H), 2.1 (m, 2H), 2.22 (t, J=6.9 Hz, 3H), 2.43 (m, 2H), 3.93 (t, 1=6.9 Hz, 2H); $^{13}$C NMR (CDCl$_3$): δ 26.8, 27.7, 33.2, 33.9, 38.2, 39.1, 43.4, 55.8, 59.4; LRMS (APIMS) (m/z) 230 (M+18) (M+NH$_4$).

3d. 2-[2-(Nitrosothio)adamantan-2-yl]ethan-1-ol

To a 0° C. cooled solution of Example 3c (1.06 g, 5 mmol) in anhydrous dichloromethane (40 mL) was added t-butyl nitrite (7.5 mmol, 890 μL). The reaction mixture was stirred at 0° C. for 30 minutes and then at room temperature for 30 minutes. The solvent was removed at reduced pressure and product was recrystallized from ethyl ether/hexane to give 1.2 g (80% yield) of the title compound as a green crystalline solid, mp 77–79° C.; $^1$H NMR (CDCl$_3$): δ 1.7–1.74 (m, 2H), 1.83–1.93 (m, 5H), 2.06 (m, 3H), 2.42–2.53 (m, 4H), 2.99 (t, J=7.3 Hz, 2H), 3.83 (t, J=7.6 Hz, 2H); $^{13}$C NMR (CDCl$_3$): δ 27.3, 27.4, 33.2, 33.9, 35.6, 38.97, 39.96, 59.1, 68.2; LRMS (APIMS) (m/z) 259 (M+18) (M+NH$_4$).

3e. 2-[2-(nitrosothio)adamanta-2-yl]ethyl chlorooate

An ice-cooled solution of 20% phosgene in toluene (2.5 ml, 5.4 mmol) was added dropwise to a solution of Example 3d (0.41 g, 1.7 mmol) and pyridine (0.138 ml, 1.7 mmol) in dichloromethane (4 ml). After stirring at 0° C. for 20 min, the reaction was concentrated using a rotary evaporator. To the residue was added dry ether (20 ml). The reaction mixture was filtered, washed with ether (2×5 ml) and the organic layer was concentrated under vacuum to gave the crude product, which was used immediately for next step.

3f. 2-[2-(Nitrosothio)adamantan-2-yl]ethyl 2-({[3-methyl-4-(2,2,2-trifluoroethoxy)-2-pyridyl]methyl}sulfinyl)benzimidazolecarboxylate Lansoprazole (0.50 g, 1.35 mmol) was added to a suspension of sodium hydride (39 mg, 1.63 mmol) in N,N-dimethylformamide (3 ml) at room temperature. The resulting clear solution was cooled in an ice bath. A solution of Example 3e in N,N-dimethylformamide (3 ml) was then added. After stirring at 0° C. for 30 min, the reaction mixture was diluted with ethyl ether/ethyl acetate (3:2 v/v) (70 ml) and washed with water (2×30 ml) and then brine (20 ml). The combined organic extracts were dried over $Na_2SO_4$ and evaporated under vacuum. The residue was purified by flash chromatography ($SiO_2$, 4/1 to 3/1 dichloromethane/acetone) to give the title compound as a green solid (0.52 g, 60.3%). Mp. 125–130° C. (dec.)(at 116° C. it started to shrink). $^1H$ NMR (300 M, $CDCl_3$) δ 8.06 (d, J=5.6 Hz, 1H), 7.90 (d, J=7.5 Hz, 1H), 7.82 (d, J=7.7 Hz, 1H), 7.487.38 (in, 2H), 6.56 (d, J=5.6 Hz, 1H), 4.78 (d, J=13 Hz, 1H), 4.75 (t, j=7.8 Hz, 2H), 4.67 (d, J=13 Hz, 1H), 4.37 (q, J=7.8 Hz, 2H), 3.37 (t, J=7.8 Hz, 2H), 2.60}2.46 (in, 4H), 2.35 (s, 3H), 2.17–1.76 (m, 10H); $^{13}C$ NMR (75 MHz, $CDCl_3$) δ 161.74, 156.92, 151.19, 149.65, 147.94, 142.77, 133.54, 126.50, 125.24, 124.55, 121.38, 114.61, 105.66, 67.04, 65.88, 65.36 (q, 3=36 Hz), 59.45, 38.74, 35.68, 35.58, 35.52, 33.73, 33.10, 33.08, 27.26, 27.11, 11.37; MS (m/e): 637 (M+1).

EXAMPLE 4

Comparative In Vivo Gastric Lesion Activity

The ethanol/HCl mixture-induced gastric lesion test in rats described by Takeuchi et al, *J. Pharmacol. Exp. Ther.,* 286: 115–121 (1998), was used to evaluate gastric lesion activity. Male Sprague Dawley rats (Charles River Laboratories, Wilmington, Mass.) weighing 230–250 g were used for the experiments. The rats were housed with laboratory chow and water ad libitum prior to the study. The rats were fasted for 24 hours with free access to water and then dosed by oral gavage with vehicle or with the test compounds given at a volume of 0.5 ml/100 g body weight. Thirty minutes after oral dosing all the rats received 1 ml of a solution of 60% ethanol in 150 mM HCl intragastrically. Food was withheld after dosing. Sixty minutes after ethanol/HCl, rats were euthanized by precharged $CO_2$. The stomachs were dissected along the greater curvature, washed with a directed stream of 0.9% saline and pinned open on a sylgard based petri dish for examination of the hemorrhagic lesions. Gastric lesion score was expressed in mm and calculated by summing the length of each lesion as described by Al-Ghamdi et al, *J. Int. Med. Res.,* 19: 2242 (1991). Results are expressed as the mean±standard error of the mean. Statistical analysis were conducted using ANOVA test followed by a Student-Newman-Keuls post-hoc test using the Abacus Concepts, Super Anova computer program (Abacus Concepts, Inc., Berkeley, Calif.).

FIG. 1 compares the gastric lesion activity of vehicle alone, lanzoprazole in vehicle and Example 2 (nitrosylated lanzoprazole) in vehicle. Ethanol/HCl mixture produced gastric lesion in the control rats treated with vehicle (0.5% Methocel). Lanzoprazole at a dose of 200 μmol/kg failed to significantly inhibit the formation of gastric lesions. The nitrosylated lanzoprazole derivative of Example 2, at 200 μmol/kg, significantly inhibited the formation of gastric lesions produced by the ethanol/HCl mixture.

The disclosure of each patent, patent application and publication cited or described in the present specification is hereby incorporated by reference herein in its entirety.

Although the invention has been set forth in detail, one skilled in the art will appreciate that numerous changes and modifications can be made to the invention, and that such changes and modifications can be made without departing from the spirit and scope of the present invention.

What is claimed is:

1. A method for treating Crohn's disease, ulcerative colitis, a peptic ulcer, a stress ulcer, a bleeding peptic ulcer, a duodenal ulcer, infectious enteritis, colitis, diverticulitis, gastric hyperacidity, dyspepsia, gastroparesis, Zollinger-Ellison syndrome, gastroesophageal reflux disease, a *Helicobacter Pylori* associated disease, short-bowel syndrome, or a hypersecretory state associated with systemic mastocytosis or basophilic leukemia and hyperhistaminemia; for facilitating ulcer healing, or for decreasing the recurrence of an ulcer in a patient in need thereof comprising administering to the patient a therapeutically effective amount of at least one proton pump inhibitor or a pharmaceutically acceptable salt thereof, and at least one compound that donates, transfers or releases nitric oxide, induces the production of endogenous nitric oxide or endothelium-derived relaxing factor, stimulates endogenous synthesis of nitric oxide or is a substrate for nitric oxide synthase.

2. A method for decreasing or reversing gastrointestinal toxicity or facilitating ulcer healing resulting from administration of a nonsteroidal antiinflammatory drug and/or a selective COX-2 inhibitor to a patient comprising administering to a patient in need thereof a therapeutically effective amount of at least one proton pump inhibitor compound, and at least one compound that donates, transfers or releases nitric oxide, induces the production of endogenous nitric oxide or endothelium-derived relaxing factor, stimulates endogenous synthesis of nitric oxide or is a substrate for nitric oxide synthase, and, optionally, at least one nonsteroidal antiinflammatory drug and/or selective COX-2 inhibitor, wherein the at least one compound that donates, transfers or releases nitric oxide, induces the production of endogenous nitric oxide or endothelium-derived relaxing factor, stimulates endogenous synthesis of nitric oxide or is a substrate for nitric oxide synthase and the at least one nonsteroidal antiinflammatory drug and/or selective COX-2 inhibitor are at least two different compounds.

3. A method for treating an infection caused by *Helicobacter pylori* comprising administering to a patient in need thereof a therapeutically effective amount of at least one acid degradable antibacterial compound, at least one proton pump inhibitor compound or a pharmaceutically acceptable salt thereof, and at least one compound that donates, transfers or releases nitric oxide, induces the production of endogenous nitric oxide or endothelium-derived relaxing factor, stimulates endogenous synthesis of nitric oxide or is a substrate for nitric oxide synthase.

4. A method for treating Crohn's disease, ulcerative colitis, a stress ulcer, infectious enteritis, colitis, diverticulitis, gastric hyperacidity, gastroparesis, Zollinger-Ellison syndrome, gastroesophageal reflux disease, a *Helicobacter Pylori* associated disease, short-bowel syndrome, or a hypersecretory state associated with systemic mastocytosis or basophilic leukemia and hyperhistaminemia in a patient in need thereof comprising administering to the patient a therapeutically effective amount of at least one proton pump inhibitor or a pharmaceutically acceptable salt thereof, and at least one compound that donates, transfers or releases nitric oxide, induces the production of endogenous nitric oxide or endothelium-derived relaxing factor, stimulates endogenous synthesis of nitric oxide or is a substrate for nitric oxide synthase.

5. The method of claim 1, further comprising administering at least one antacid.

6. The method of claim 1, 2, 3, or 4, wherein the at least one proton pump inhibitor compound is a substituted benzimidazole, a substituted quinoline, a substituted pyrimidine, a substituted thiadiazole, a substituted sulfinylnicotinamide, a substituted thienoimidazole, or a substituted imidazopyridine.

7. The method of claim 6, wherein the substituted benzimidazole is omeprazole, lansoprazole, pantoprazole, rabeprazole, leminoprazole, timoprazole, tenatoprazole, disulprazole, esomeprazole, 2-(2-benzimidazolyl)pyridine, a tricyclic imidazole, a thienopydidine benzimidazole, a fluoroalkoxy substituted benzimidazole, a dialkoxy benzimidazole, a N-substituted 2-(pyridylalkenesulfinyl) benzimidazole, a cycloheptenepyridine, a 5-pyrrolyl-2-pyridylmethylsulfinyl benzimidazole, a alkylsulfinyl benzimidazole, a fluoro-pyridylmethylsulfinyl benzimidazole, an imidazo(4.5-b)pyridine, RO 18-5362 or IY 81149; wherein the substituted quinoline is a 4-amino-3-carbonyl quinoline, a 4-amino-3-acylnaphthyride, a 4-aminoquinoline, a 4-amino-3-acylquinoline or a 3-butyryl-4-(2-methylphenylamino)-8-(2-hydroxyethoxy) quinoline; wherein the substituted pyrimidine is a substituted quinazoline, a tetrahydroisoquinolin-2-yl pyrimidine or YH 1885; wherein the substituted thiadiazole is 3-substituted 1,2,4-thiadiazolo(4,5-a) benzimidazole or a 3-substituted imidazo(1,2-d)-thiadiazole; wherein the substituted sulfinylnicotinamide is a 2-sulfinylnicotinamide; wherein the substituted thienoimidazole is a pyridylsulfinylbenzimidazole, a pyridylsulfinyl thieno imidazole, a theinoimidazole-toluidine, a 4,5-dihydrooxazole, a thienoimidazole-toluidine or Hoe-731; wherein the substituted imidazopyridine is a imidazo(1,2-a) pyridine, a pyrrolo(2,3-b)pyridine or a pharmaceutically acceptable salt thereof.

8. The method of claim 7, further comprising administering a pharmaceutically acceptable carrier.

9. The method of claim 1, 2, 3, or 4, wherein the compound that donates, transfers or releases nitric oxide, induces the production of endogenous nitric oxide or endothelium-derived relaxing factor, stimulates endogenous synthesis of nitric oxide or is a substrate for nitric oxide synthase is an S-nitrosothiol.

10. The method of claim 9, wherein the S-nitrosothiol is S-nitroso-N-acetylcysteine, S-nitroso-captopril, S-nitroso-N-acetylpenicillanine, S-nitroso-homocysteine, S-nitroso-cysteine or S-nitroso-glutathione.

11. The method of claim 9, wherein the S-nitrosothiol is:
   (i) HS(C($R_e$)($R_f$))$_m$SNO;
   (ii) ONS(C($R_e$)($R_f$))$_m R_e$; or
   (iii) H$_2$N—CH(CO$_2$H)—(CH$_2$)$_m$—C(O)NH—CH (CH$_2$SNO)—C(O)NH—CH$_2$—CO$_2$H;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or (C($R_e$)($R_f$))$_k$—T—Q, or $R_e$ and $R_f$ taken together with the carbons to which they are attached form a carbonyl, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or —N($R_a$)$R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$C(T—Q)($R_e$) ($R_f$), or —(N$_2$O$_2$—)$^-$.M$^+$, wherein M$^+$ is an organic or inorganic cation; with the proviso that when $R_i$ is —CH$_2$—C(T—Q)($R_e$)($R_f$) or —(N$_2$O$_2$—).M$^+$; then "—T—Q" can be a hydrogen, an alkyl group, an alkoxyalkyl group, an aminoalkyl group, a hydroxy group or an aryl group.

12. The method of claim 1, 2, 3 or 4, wherein the at least one proton pump inhibitor compound or the pharmaceutically acceptable salt thereof, and the at least one compound that donates, transfers or releases nitric oxide, induces the production of endogenous nitric oxide or endothelium-derived relaxing factor, stimulates endogenous synthesis of nitric oxide or is a substrate for nitric oxide synthase are administered separately.

13. The method of claim 1, 2, 3 or 4, wherein the at least one proton pump inhibitor compound or the pharmaceutically acceptable salt thereof, and the at least one compound that donates, transfers or releases nitric oxide, induces the production of endogenous nitric oxide or endothelium-derived relaxing factor, stimulates endogenous synthesis of nitric oxide or is a substrate for nitric oxide synthase are administered together in the form of a composition.

14. The method of claim 1, 2, 3 or 4, wherein the at least one proton pump inhibitor compound or a pharmaceutically acceptable salt thereof, and the at least one compound that donates, transfers or releases nitric oxide, induces the production of endogenous nitric oxide or endothelium-derived relaxing factor, stimulates endogenous synthesis of nitric oxide or is a substrate for nitric oxide synthase are administered orally, bucally topically, by injection, by inhalation, or by transdermal application.

15. The method of claim 14, wherein the at least one proton pump inhibitor compound or a pharmaceutically acceptable salt thereof, and the at least one compound that donates, transfers or releases nitric oxide, induces the production of endogenous nitric oxide or endothelium-derived relaxing factor, stimulates endogenous synthesis of nitric oxide or is a substrate for nitric oxide synthase are administered orally in a solid dosage form or a liquid dosage form.

16. The method of claim 15, wherein the solid dosage form is a capsule, a tablet, an effervescent tablet, a chewable tablet, a pill, a powder, a sachet, a granule or a gel.

17. The method of claim 15, wherein the liquid dosage form is an emulsion, a solution, a suspension, a syrup, or an elixir.

18. A method for decreasing or reversing gastrointestinal toxicity or facilitating ulcer healing resulting from administration of a nonsteroidal antiinflammatory drug and/or a selective COX-2 inhibitor in a patient in need thereof comprising administering a therapeutically effective amount of at least one proton pump inhibitor compound and at least one S-nitrosothiol.

19. The method of claim 18, further comprising administering a therapeutically effective amount of at least one nonsteroidal antiinflammatory drug and/or selective COX-2 inhibitor.

20. A method for treating an ulcer in a patient in need thereof comprising administering a therapeutically effective amount of at least one proton pump inhibitor and at least one S-nitrosothiol.

21. The method of claim 20, wherein the ulcer is a peptic ulcer, a stress ulcer, a bleeding peptic ulcer, a duodenal ulcer, or gastritis.

22. A method for treating Crohn's disease, ulcerative colitis, a peptic ulcer, a stress ulcer, a bleeding peptic ulcer, a duodenal ulcer, infectious enteritis, colitis, diverticulitis, gastric hyperacidity, dyspepsia, gastroparesis, Zollinger-Ellison syndrome, gastroesophageal reflux disease, a *Helicobacter Pylori* associated disease, short-bowel syndrome, or a hypersecretory state associated with systemic mastocytosis or basophilic leukemia and hyperhistaminemia; for facilitating ulcer healing, or for decreasing the recurrence of an ulcer in a patient in need thereof comprising administering to the patient a therapeutically effective amount of at least one proton pump inhibitor or a pharmaceutically acceptable salt thereof, and at least one S-nitrosothiol.

23. The method of claim 18, 20 or 22, wherein the S-nitrosothiol is S-nitroso-N-acetylcysteine, S-nitroso-captopril, S-nitroso-N-acetylpenicillamine, S-nitroso-homocysteine, S-nitroso-cysteine or S-nitroso-glutathione.

24. The method of claim 18, 20 or 22, wherein the S-nitrosothiol is:

(i) $HS(C(R_e)(R_f))_m SNO$;

(ii) $ONS(C(R_e)(R_f))_m R_e$; or (iii) $H_2N—CH(CO_2H)—(CH_2)_m—C(O)NH—CH(CH_2SNO)—C(O)NH—CH_2—CO_2H$;

wherein m is an integer from 2 to 20; $R_e$ and $R_r$ are each independently a hydrogen, an alkyl, a cycloalkoxy, a halogen, a hydroxy, an hydroxyalkyl, an alkoxyalkyl, an arylheterocyclic ring, an alkylaryl, a cycloalkylalkyl, a heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cycloalkylthio, a cycloalkenyl, a cyano, an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, a sulfonic ester, a urea, a phosphoryl, a nitro, —T—Q, or $(C(R_e)(R_f))_k$—T—Q, or $R_e$ and $R_f$ taken together with the carbons to which they are attached form a carbonyl, a methanthial, a heterocyclic ring, a cycloalkyl group or a bridged cycloalkyl group; Q is —NO or —NO$_2$; and T is independently a covalent bond, a carbonyl, an oxygen, —S(O)$_o$— or —N(R$_o$)R$_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an aryl carboxylic acid, an alkylcarboxylic ester, an arylcarboxylic ester, an alkylcarboxamido, an arylcarboxamido, an alkylaryl, an alkylsulfinyl, an alkylsulfonyl, an arylsulfinyl, an arylsulfonyl, a sulfonamido, a carboxamido, a carboxylic ester, an amino alkyl, an amino aryl, —CH$_2$—C(T—Q)(R$_e$)(R$_f$), or —(N$_2$O$_2$—)$^-$.M$^+$, wherein M$^+$ is an organic or inorganic cation; with the proviso that when $R_i$ is —CH$_2$—C(T—Q)(R$_e$)(R$_f$) or —(N$_2$O$_2$—)$^-$.M$^+$; then "—T—Q" can be a hydrogen, an alkyl group, an alkoxyalkyl group, an aminoalkyl group, a hydroxy group or an aryl group.

25. The method of claim 18, 20 or 22, wherein the at least one proton pump inhibitor compound is a substituted benzimidazole, a substituted quinoline, a substituted pyrimidine, a substituted thiadiazole, a substituted sulfinylnicotinamide, a substituted thienoimidazole, or a substituted imidazopyridine.

26. The method of claim 25, wherein the substituted benzimidazole is omeprazole, lansoprazole, pantoprazole, rabeprazole, leminoprazole, timoprazole, tenatoprazole, disulprazole, esomeprazole, 2-(2-benzimidazolylipyridine, a tricyclic imidazole, a thienopydidine benzimidazole, a fluoroalkoxy substituted benzimidazole, a dialkoxy benzimidazole, a N-substituted 2-(pyridylalkenesulfinyl) benzimidazole, a cycloheptenepyridine, a 5-pyrrolyl-2-pyridylmethylsulfinyl benzimidazole, a alkylsulfinyl benzimidazole, a fluoro-pyridylmethylsulfinyl benzimidazole, an imidazo(4,5-b)pydridine, RO 18-5362 or IY 81149; wherein the substituted quinoline is a 4-amino-3-carbonyl quinoline, a 4 amino-3-acylnaphthyride, a 4-aminoquinoline, a 4-amino-3-acylquinoline or a 3-butyryl-4-(2-methylphenylamino)-8-(2-hydroxyethoxy) quinoline; wherein the substituted pyrimidine is a substituted quinazoline, a tetrahydroisoquinolin-2-yl pyrimidine or YH 1885; wherein the substituted thiadiazole is 3-substituted 1,2,4-thiadiazolo(4,5-a) benzimidazole or a 3-substituted imidazo(1,2-d)thiadiazole; wherein the substituted sulfinylnicotinamide is a 2-sulfinylnicotinamide; wherein the substituted thienoimidazole is a pyridylsulfinyl-benz imidazole, a pyridylsulfinyl thieno imidazole, a theinoimidazole-toluidine, a 4,5-dihydrooxazole, a thienoimidazole-toluidine or Hoe-731; wherein the substituted imidazopyridine is a imidazo(1,2-a)pyridine, a pyrrolo (2,3-b)pyridine or a pharmaceutically acceptable salt thereof.

27. The method of claim 18, 20 or 22, wherein the at least one proton pump inhibitor compound or the pharmaceutically acceptable salt thereof, and the at least one S-nitrosothiol are administered separately.

28. The method of claim 18, 20 or 22, wherein the at least one proton pump inhibitor compound or the pharmaceutically acceptable salt thereof, and the at least one S-nitrosothiol are administered together in the form of a composition.

29. The method of claim 18, 20 or 22, wherein the at least one proton pump inhibitor compound or a pharmaceutically acceptable salt thereof, and the at least one S-nitrosothiol are administered orally, bucally, topically, by injection, by inhalation, or by transdermal application.

30. The method of claim 18, 20 or 22, wherein the at least one proton pump inhibitor compound or a pharmaceutically acceptable salt thereof, and the at least S-nitrosothiol are administered orally in a solid dosage form or a liquid dosage form.

31. The method of claim 30, wherein the solid dosage form is a capsule, a tablet, an effervescent tablet, a chewable tablet, a pill, a powder, a sachet, a granule or a gel.

32. The method of claim 30, wherein the liquid dosage form is an emulsion, a solution, a suspension, a syrup, or an elixir.

* * * * *